(12) United States Patent
Roy et al.

(10) Patent No.: US 9,872,859 B2
(45) Date of Patent: Jan. 23, 2018

(54) MATERIALS AND METHODS FOR TARGETING THERAPEUTIC COMPOSITIONS TO GUT-ASSOCIATED LYMPHOID TISSUE (GALT)

(71) Applicants: Upal Roy, Miami, FL (US); Hong Ding, Clarksville, MD (US); Madhavan Nair, Coral Gables, FL (US)

(72) Inventors: Upal Roy, Miami, FL (US); Hong Ding, Clarksville, MD (US); Madhavan Nair, Coral Gables, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/437,878

(22) Filed: Feb. 21, 2017

(65) Prior Publication Data
US 2017/0239258 A1    Aug. 24, 2017

Related U.S. Application Data

(60) Provisional application No. 62/297,835, filed on Feb. 20, 2016.

(51) Int. Cl.
*A61K 31/536* (2006.01)
*A61K 47/48* (2006.01)

(52) U.S. Cl.
CPC .......... *A61K 31/536* (2013.01); *A61K 47/488* (2013.01); *A61K 47/48215* (2013.01); *A61K 47/48561* (2013.01)

(58) Field of Classification Search
CPC ............ A61K 31/536; A61K 47/48215; A61K 47/48561; A61K 47/488
See application file for complete search history.

(56) References Cited

U.S. PATENT DOCUMENTS

2005/0244490 A1*  11/2005  Otto ..................... A61K 9/2077
                                                   424/451
2013/0236553 A1*   9/2013  Gendelman .......... A61K 9/0019
                                                   424/490

OTHER PUBLICATIONS

Lembo (Antiviral Chemistry and Chemotherapy, published 2010, pp. 53-70).*
Liu et al. (Theranostics, Published 2012, pp. 705-713).*
Ohno et al. (Gut Microbes, published 2010, pp. 407-410).*
Kovochich et al. (PLOS One, published 2011, pp. 1-8).*
Hase et al. (DNA Res., published 2005, pp. 127-137).*
Agudelo, M. et al., "Effects of Alcohol on Histone Deacetylase 2 (HDAC2) and the Neuroprotective Role of Trichostatin A (TSA)." *Alcohol Clin. Exp. Res.*, Aug. 2011, 35(8):1550-1556, doi: 10.1111/j.1530-0277.2011.01492.x.
Atluri, V.S.R. et al., "Human Synaptic Plasticity Gene Expression Profile and Dendritic Spine Density Changes in HIV-Infected Human CNS Cells: Role in HIV-Associated Neurocognitive Disorders (HAND)." *PLOS One*, Apr. 2013, 8(4):1-11, doi: 10.1371/journal.pone.0061399.
Atluri, V.S.R. et al., "Vorinostat Positively Regulates Synaptic Plasticity Genes Expression and Spine Density in HIV Infected Neurons: Role of Nicotine in Progression of HIV-Associated Neurocognitive Disorder." *Mol. Brain*, May 2014, 7(37):1-17, doi: 10.1186/1756-6606-7-37.
Best, B.M. et al., "Low Atazanavir Concentrations in Cerebrospinal Fluid." *AIDS*, Jan. 2009, 23(1):83-87, doi: 10.1097/QAD.0b013e328317a702.
Chen, L. et al., "Pluronic P105/F127 Mixed Micelles for the Delivery of Docetaxel Against Taxol-Resistant Non-Small Cell Lung Cancer: Optimization and In Vitro, In Vivo Evaluation." *Int. J. Nanomedicine*, Jan. 2013, 8:73-84, doi: 10.2147/IJN.S38221.
Dane, K.Y. et al., "Nano-Sized Drug-Loaded Micelles Deliver Payload to Lymph Node Immune Cells and Prolong Allograft Survival." *J. Control Release*, Aug. 2011, 156(2):154-160, doi: 10.1016/j.jconrel.2011.08.009.
Des Rieux, A. et al., "Transport of Nanoparticles Across an In Vitro Model of the Human Intestinal Follicle Associated Epithelium." *Eur. J. Pharm. Sci.*, Jul.-Aug. 2005, 25(4-5):455-465, doi: 10.1016/j.ejps.2005.04.015.
Dhoro, M. et al., "CYP2B6*6, CYP2B6*18, Body Weight and Sex are Predictors of Efavirenz Pharmacokinetics and Treatment Response: Population Pharmacokinetic Modeling in an HIV/AIDS and TB Cohort in Zimbabwe," *BMC Pharmacol. Toxicol.*, Mar. 2015, 16(4):1-10, doi: 10.1186/s40360-015-0004-2.
Ding, H. et al., "Bioconjugated PLGA-4-arm-PEG Branched Polymeric Nanoparticles as Novel Tumor Targeting Carriers." *Nanotechnology*, 2011;22(16):1-13, doi: 10.1088/0957-4484/22/16/165101.
Ding, H. et al., "Enhanced Blood-Brain Barrier Transmigration Using a Novel Transferrin Embedded Fluorescent Magnetoliposome Nanoformulation." *Nanotechnology*, Feb. 2014, 25(5):1-30. doi: 10.1088/0957-4484/25/5/055101.
Ding, H. et al., "Gold Nanorods Coated with Multilayer Polyelectrolyte as Contrast Agents for Multimodal Imaging." *J. Phys. Chem. C.*, Jun. 2007, 111(34):12552-12557, doi: 10.1021/jp0733419.
Ding, H., Wu, F., "Image Guided Biodistribution and Pharmacokinetic Studies of Theranostics." *Theranostics*, Nov. 2012, 2(11):1040-1053, doi: 10.7150/thno.4652.

(Continued)

*Primary Examiner* — Alma Pipic
(74) *Attorney, Agent, or Firm* — Saliwanchik, Lloyd & Eisenschenk

(57) ABSTRACT

The present invention provides novel, long-acting nanoformulated drugs and targeted drug delivery methods, and uses thereof. In one embodiment, the nanoformulated drug is a retroviral drug. In one embodiment, the nanoformulated composition comprises a nanocarrier with one or more incorporated drugs. In an exemplary embodiment, the drug is efavirenz (EFV). In a further embodiment, the nanocarrier is associated with an agent for targeting microfold cells (M-cells). In a specific embodiment, the targeting agent binds to an M-cell marker known as glycoprotein 2 (GP2). Via this mechanism, the nanodrug is targeted toward GALT.

19 Claims, 10 Drawing Sheets

(56) References Cited

OTHER PUBLICATIONS

Ding, H. Wu F., "Image Guided Biodistribution of Drugs and Drug Delivery." *Theranostics*, Nov. 2012, 2(11):1037-1039, doi: 10.7150/thno.5321.

Ding, H. et al., "Image-Guided Drug Delivery to the Brain Using Nanotechnology." *Drug Discov. Today*, Nov. 2013, 18(21-22):1074-1080, doi: 10.1016/j.drudis.2013.06.010.

Ding, H, et al., "Non-Invasive Tumor Detection in Small Animals Using Novel Functional Pluronic Nanomicelles Conjugated with Anti-Mesothelin Antibody." *Nanoscale*, Feb. 2011, 3(4):1813-1822, doi: 10.1039/c1nr00001b.

Du, B. et al., "Preparation, Characterization and In Vivo Evaluation of 2-Methoxyestradiol-Loaded Liposomes." *Int. J. Pharm.*, Jan. 2010, 384(1-2):140-147, doi: 10.1016/j.ijpharm.2009.09.045.

Eifler, A.C., Thaxton, C.S., "Nanoparticle Therapeutics: FDA Approval, Clinical Trials, Regulatory Pathways, and Case Study." *Methods Mol. Biol.*, Apr. 2011, 726:Abstract, doi: 10.1007/978-1-61779-052-2.

Elluru, M. et al., "Synthesis and Characterization of Biocompatible Hydrogel Using Pluronics-Based Block Copolymers." *Polymer*, Feb. 2013, 54(8):2088-2095, doi: 10.1016/j.polymer.2013.02.017.

Gandhi, N. et al., "Interactive Role of Human Immunodeficiency Virus Type 1 (HIV-1) Clade-Specific Tat Protein and Cocaine in Blood—Brain Barrier Dysfunction: Implications for HIV-1-Associated Neurocognitive Disorder." *J. Neurovirol.*, May 2010, 16(4):294-305, doi: 10.3109/13550284.2010.499891.

Gullberg, E. et al., "Expression of Specific Markers and Particle Transport in a New Human Intestinal M-Cell Model." *Biochem. Biophys. Res. Commun.*, Nov. 2000, 279(3):808-813, doi: 10.1006/bbrc.2000.4038.

Haney, M.J. et al., "Blood-Borne Macrophage-Neural Cell Interactions Hitchhike Endosome Networks for Cell-Based Nanozyme Brain Delivery." *Nanomedicine*, Jun. 2012, 7(6):815-833, doi: 10.2217/nnm.11.156.

Hase, K. et al., "Uptake Through Glycoprotein 2 of FimH$^+$ Bacteria by M Cells Initiates Mucosal Immune Response." *Nature*, Nov. 2009, 462(7270):226-230, doi: 10.1038/nature08529.

Hondo, T. et al., "Cytokeratin 18 is a Specific Marker of Bovine Intestinal M Cell." *Am. J. Physiol. Gastrointest Liver Physiol.*, Mar. 2011, 300(3):G442-G453, doi: 10.1152/ajpgi.00345.2010.

Hua, S., "Comparison of In Vitro Dialysis Release Methods of Loperamide-Encapsulated Liposomal Gel for Topical Drug Delivery." *Int. J. Nanomedicine*, Jan. 2014, 9:735-744, doi: 10.2147/IJN.S55805.

Kanmogne, G.D. et al., "Mononuclear Phagocyte Intercellular Crosstalk Facilitates Transmission of Cell-Targeted Nanoformulated Antiretroviral Drugs to Human Brain Endothelial Cells." *Int. J. Nanomedicine*, May 2012, 7:2373-2388, doi: 10.2147/IJN.S29454.

Kerneis, S. et al., "Conversion by Peyer's Patch Lymphocytes of Human Enterocytes into M Cells that Transport Bacteria." *Science*, Aug. 1997, 277(5328):949-952, doi: 10.1126/science.277.5328.949.

Kunisawa, J. et al., "Gut-Associated Lymphoid Tissues for the Development of Oral Vaccines." *Adv. Drug Deliv. Rev.*, May 2012, 64(6):523-530, doi: 10.1016/j.addr.2011.07.003.

Lerner, P. et al., "The Gut Mucosal Viral Reservoir in HIV-Infected Patients is not the Major Source of Rebound Plasma Viremia Following Interruption of Highly Active Antiretroviral Therapy." *J. Virol.*, May 2011, 85(10):4772-4782, doi: 10.1128/JVI.02409-10.

Li, S. et al., "In-Vitro and In-Vivo Evaluation of Austocystin D Liposomes." *J. Pharm. Pharmacol.*, Mar. 2013, 65(3):355-362, doi: 10.1111/j.2042-7158.2012.01606.x.

Manocha, M. et al., "Enhanced Mucosal and Systemic Immune Response with Intranasal Immunization of Mice With HIV Peptides Entrapped in PLG Microparticles in Combination With *Ulex Europaeus-I* Lectin as M Cell Target." *Vaccine*, Jul. 2005, 23(48-49):5599-5617, doi: 10.1016/j.vaccine.2005.06.031.

Oerlemans, C. et al., "Polymeric Micelles in Anticancer Therapy: Targeting, Imaging and Triggered Release." *Pharm. Res.*, Aug. 2010, 27(12):2569-2589, doi: 10.1007/s11095-010-0233-4.

Oikonomou, E. et al., "BRAF$^{V600E}$ Efficient Transformation and Induction of Microsatellite Instability Versus KRAS$^{G12V}$ Induction of Senescence Markers in Human Colon Cancer Cells." *Neoplasia*, Nov. 2009, 11(11):1116-1131, doi: 10.1593/neo.09514.

Olagunju, A. et al., "Breast Milk Pharmacokinetics of Efavirenz and Breastfed Infants' Exposure in Genetically Defined Subgroups of Mother-Infant Pairs: An Observational Study." *Clin. Infect. Dis.*, Apr. 2015, 61(3):453-463, doi: 10.1093/cid/civ317.

Pilakka-Kanthikeel, S. et al., "Targeted Brain Derived Neurotropic Factors (BDNF) Delivery Across the Blood—Brain Barrier for Neuro-Protection Using Magnetic Nano Carriers: An In-Vitro Study." *PLOS One*, Apr. 2013, 8(4):1-10, doi: 10.1371/journal.pone.0062241.

Reddy, S.T., "In Vivo Targeting of Dendritic Cells in Lymph Nodes With Poly(Propylene Sulfide) Nanoparticles." *J. Control. Release*, Mar. 2006, 112(1):26-34, doi: 10.1016/j.jconrel.2006.01.006.

Roy, U. et al., "Specific Increase in MDR1 Mediated Drug-Efflux in Human Brain Endothelial Cells Following Co-Exposure to HIV-1 and Saquinavir." *PLOS One*, Oct. 2013, 8(10):1-11, doi: 10.1371/journal.pone.0075374.

Schmidtmayerova, H. et al., "Human Immunodeficiency Virus Type 1 T-Lymphotropic Strains Enter Macrophages Via a CD4- and CXCR4-Mediated Pathway: Replication is Restricted at a Postentry Level." *J. Virol.*, Mar. 1998, 72(6):4633-4642.

Simon, T. et al., "Gold-Pluronic Core-Shell Nanoparticles: Synthesis, Characterization and Biological Evaluation." *J. Nanopart. Res.*, Mar. 2013, 15(4):1-8, doi: 10.1007/s11051-013-1578-5.

Tahoun, A. et al., "*Salmonella* Transforms Follicle-Associated Epithelial Cells into M Cells to Promote Intestinal Invasion." *Cell Host & Microbe*, Nov. 2012, 12(5):645-656, doi: 10.1016/j.chom.2012.10.009.

Tan, R. et al., "Preparation of Vincristine Sulfate-Loaded Poly (Butylcyanoacrylate) Nanoparticles Modified with Pluronic F127 and Evaluation of Their Lymphatic Tissue Targeting." *J. Drug Target.*, Jul. 2014, 22(6):509-517, doi: 10.3109/1061186X.2014.897708.

Torchilin, V.P., "Multifunctional Nanocarriers." *Adv. Drug Deliv. Rev.*, Sep. 2006, 58(14):1532-1555, doi: 10.1016/j.addr.2006.09.009.

Wallace, S.J. et al., "Drug Release from Nanomedicines: Selection of Appropriate Encapsulation and Release Methodology." *Drug Deliv. Transl. Res.*, Aug. 2012, 2(4):284-292, doi: 10.1007/s13346-012-0064-4.

Wu, F. et al., "Noninvasive Real-Time Fluorescence Imaging of the Lymphatic Uptake of BSA-IRDye 680 Conjugate Administered Subcutaneously in Mice." *J. Pharm. Sci.*, Jan. 2012, 101(5):1744-1754, doi: 10.1002/jps.23058.

Yang, S.P. et al., "Effectiveness of a Reduced Dose of Efavirenz Plus 2 NRTIs as Maintenance Antiretroviral Therapy With the Guidance of Therapeutic Drug Monitoring." *J. Int. AIDS Soc.*, Nov. 2014, 17(3):Abstract.

Yuki, Y. et al., "Progress Towards an AIDS Mucosal Vaccine: An Overview." *Tuberculosis*, Aug. 2007, 87(1):S35-S34, doi: 10.1016/j.tube.2007.05.005.

\* cited by examiner

MATERIALS AND METHODS FOR TARGETING THERAPEUTIC COMPOSITIONS TO GUT-ASSOCIATED LYMPHOID TISSUE (GALT)

CROSS-REFERENCE TO RELATED APPLICATION(S)

The present application claims the benefit of U.S. Provisional Application Ser. No. 62/297,835, filed Feb. 20, 2016, which is hereby incorporated by reference herein in its entirety, including any figures, tables, nucleic acid sequences, amino acid sequences, or drawings.

BACKGROUND OF INVENTION

The Human Immunodeficiency Virus 1 (HIV-1) still remains one of the leading life-threatening diseases in the world. Subsequent to the introduction of combination antiretroviral therapy (ART), HIV-infection-related morbidity and mortality have dramatically decreased; however, currently available antiretroviral agents, such as those involved in highly active antiretroviral therapy (HAART), are only capable of controlling HIV replication, rather than completely eradicating virus from patients. As a result, HIV infection has now become a chronic disease requiring a lifelong commitment to daily oral treatment.

HAART comprises complex regimens that require strict adherence to complicated treatment schedules, and the quality of treatment depends on the patient's adherence to the recommended regimens. Antiretroviral adherence is the second strongest predictor of progression to AIDS and death, after CD4 count (Garcia de Olalla, P. et al., *J Acquir Immune Defic Syndr.* 2002; 30(1):105-110; Nowacek, A. et al., Nanomedicine (Lond). 2009; 4(5):557-574).

Currently HAART only helps in suppressing HIV replication and does not clear virus from infected individuals. Various reservoirs of replication-competent HIV have been identified that may contribute to this persistence.

Most antiretroviral drugs have a short half-life and, in turn, need to be in circulation constantly to control the virus replication. As a result, it is believed that missing a medication dose even once can provide an opportunity for viruses to replicate such that a medication-resistant HIV strain may develop.

Long-acting formulations of therapeutic agents have been used to improve adherence and prevent issues such as missing doses or treatment fatigue to prescribed medication in a number of different fields such as contraception, male hypogonadism, and schizophrenia, with demonstrable success (Boffito, M. et al., *Drugs.* 2014; 74(1):7-13). Thus, it has been suggested that development of similar approaches in reducing the impact of individual adherence could increase the efficacy of treatment strategies for HIV-AIDS.

Efavirenz (EFV) is a non-nucleoside reverse transcriptase inhibitor (NNRTI) being used as part of HAART for the treatment of HIV-1. Although it is always given in combination with other drugs to treat HIV infection, the low efficacy is still a main concern for this drug. The low efficacy is due to its poor aqueous solubility, low bioavailability, and resistance profile.

The gastrointestinal tract plays a key role in not only early HIV infection in establishing viral reservoirs in gut-associated lymphoid tissue (GALT) but also disease pathology. The epithelium that lines the human gut is impermeable to macromolecules/microorganisms except Peyer's patches, where the follicle-associated epithelium contains microfold cells (M-cells). M-cells are specialized epithelial cells that are predominantly present in the GALT. Many pathogenic organisms exploit M-cells to cross the digestive epithelial barrier[10].

Many different treatment options have been proposed to eradicate the virus from GALT; however, due to the complex physiology involved, it is difficult to design drugs that are targeted toward GALT.

Therefore, the identification of means to improve the bioavailability and therapeutic index of HAART drugs to eradicate the GALT reservoir is of great importance.

BRIEF SUMMARY

The present invention provides novel, long-acting nanoformulated drugs and targeted drug delivery methods, and uses thereof. In one embodiment, the nanoformulated drug is a retroviral drug.

In one embodiment, the nanoformulated composition comprises a nanocarrier with one or more incorporated drugs. The drug can be any drug. Specifically exemplified herein are drugs for treating retrovirus infections, including, for example, HIV. In an exemplary embodiment, the drug is efavirenz (EFV). In a further exemplary embodiment the treatment is for a viral infection, which may be latent or active.

In a further embodiment, the nanocarrier is associated with an agent for targeting microfold cells (M-cells). In a specific embodiment, the targeting agent binds to an M-cell marker known as glycoprotein 2 (GP2) antibody. Via this mechanism, the nanodrug is targeted toward GALT.

In specific embodiments, the nanocarrier is a poloxamer. Specific poloxamers are also known by the trade names Synperonics®, Pluronics®, and Kolliphor®. In a specific embodiment, the poloxamer is the carboxylated Pluronic® block copolymer abbreviated F127COOH.

Advantageously, the formulation of the current invention reduces or prevents enzymatic digestion and facilitates drug uptake at desired tissue and cells.

In certain embodiments, the composition is administered orally. In one embodiment, the nanoformulation is encapsulated into an enteric coated capsule for in vivo drug delivery targeted to GALT. Advantageously, the formulation will sustain stomach digestion due to encapsulation and release in the gut because of pH difference. Once it is released, it will bind to M-cells and incorporated to GALT where it will facilitates sustained release of the incorporated drug.

In accordance with the present invention, a nanoformulated drug can be delivered to an animal conveniently, e.g., by oral administration, and can be directed to the desired target at a high rate and with a high ratio of transfer of the drug from the site of administration to the site of pharmacological effect.

In one embodiment, the method of the invention comprises the steps of preparing the nanodrug composition with at least one drug, administering the nanodrug composition to an animal in a manner that allows the drug to reach a target area, and allowing the drug to be released from the carrier to achieve the desired pharmacological effect in a sustained manner.

In a specific embodiment, the nanodrug composition is a polymer-based Pluronic® nanocarrier containing an anti-HIV drug (e.g., efavirenz (EFV)) targeting microfold cells (M-cell) in the GALT.

(F127COOH). (1B) The Efavirenz loaded F127COOH micelles bioconjugated with antibody.

Figure 2A:
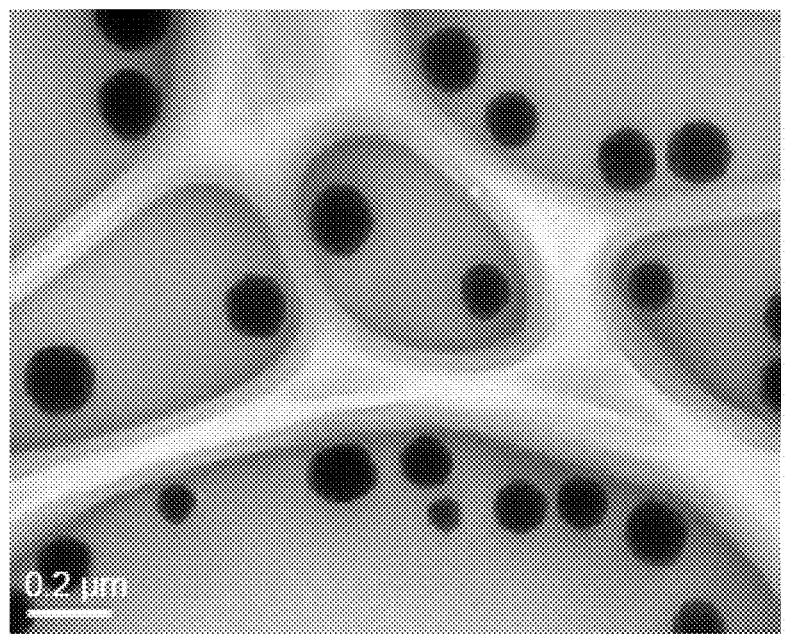
Figure 2B:
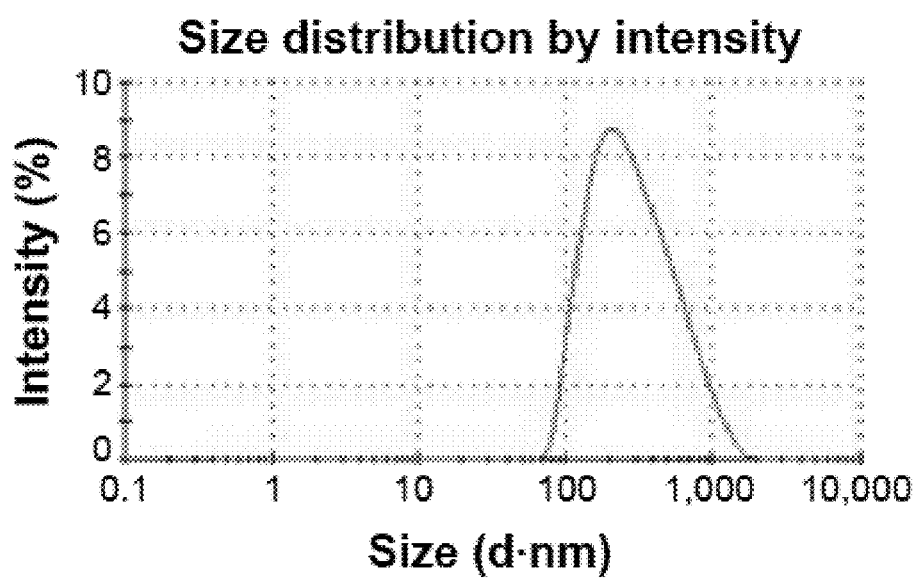

FIGS. 2A-2B. (2A) Transmission Electron Microscopy (TEM) and (2B) Dynamic Laser Scattering (DLS) of a formulation of the current invention. 2A shows the representative particle shape and size of a F127COOH-EFV nanodrug to be around 120-140 nm using the TEM technique, which also shows excellent mono-dispersion directly. 2B shows the hydrodynamic radius of F127COOH-EFV nanodrug particles in an aqueous solution about 130 nm using DLS technique with small size distribution index (PDI) as 0.10. The hydrodynamic size in aqueous dispersion by method of DLS is consistent with TEM results.

Figure 3A:
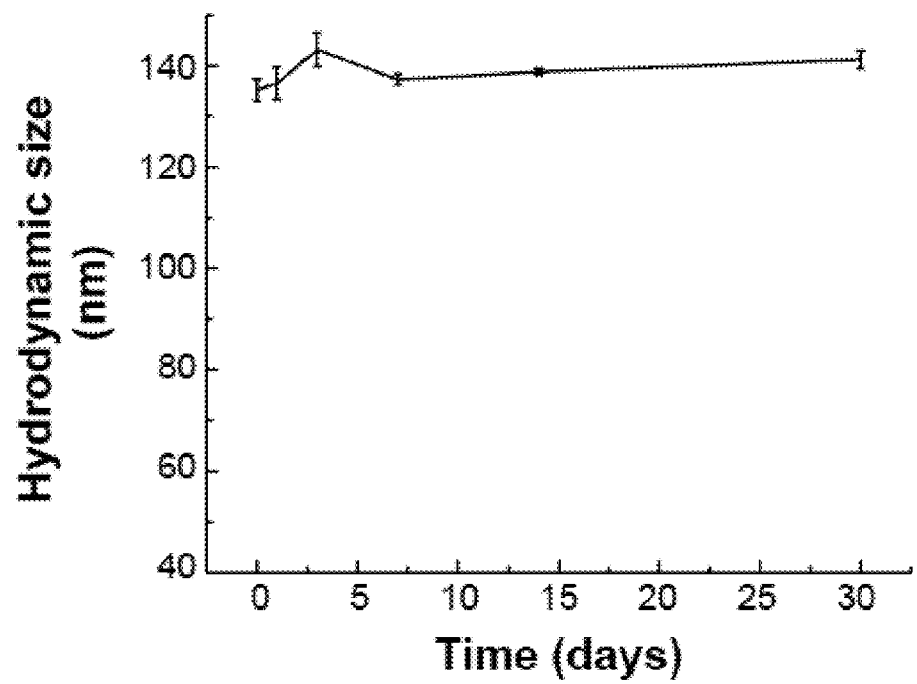
Figure 3B:
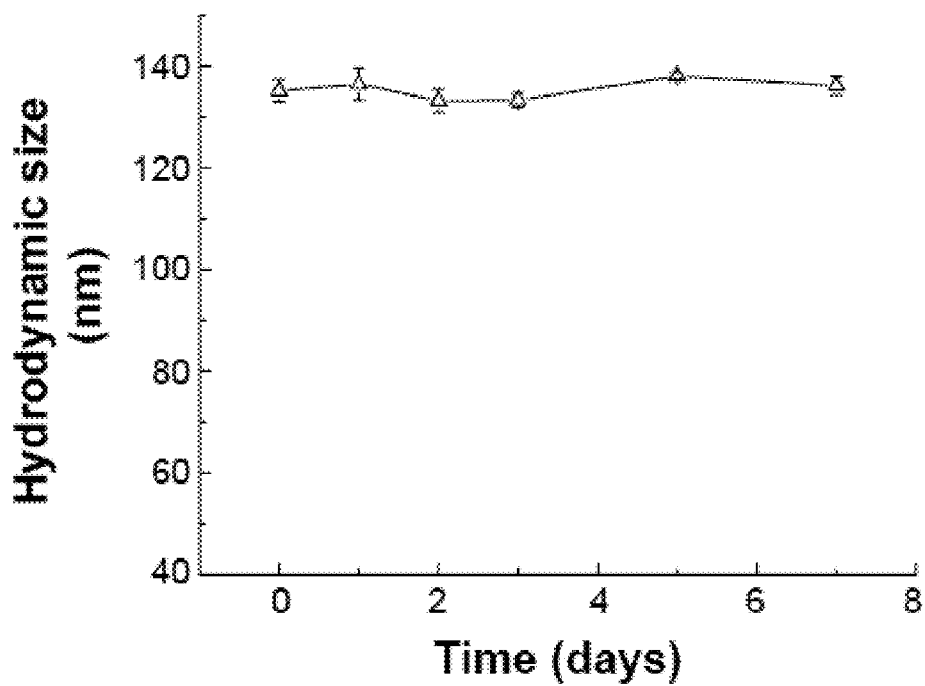

FIGS. 3A-3B. Stability characterization of the nanoformulation (A: pH 7.4 phosphate buffered saline (PBS); B: 0.005% pepsin solution). (3A) DLS Hydrodynamic size against time indicated the long-term stability of nanodrug in aqueous solution. Both of them showed size fluctuation <10%. Hydrodynamic diameter of F127COOH-EFV presented size fluctuation <10% indicating the long-term well colloidal stability in a physiological condition (pH 7.4). (3B) One week incubation with 0.005% pepsin solution showed the stability of nanoformulation under intestine enzymatic circumstance.

Figure 4:
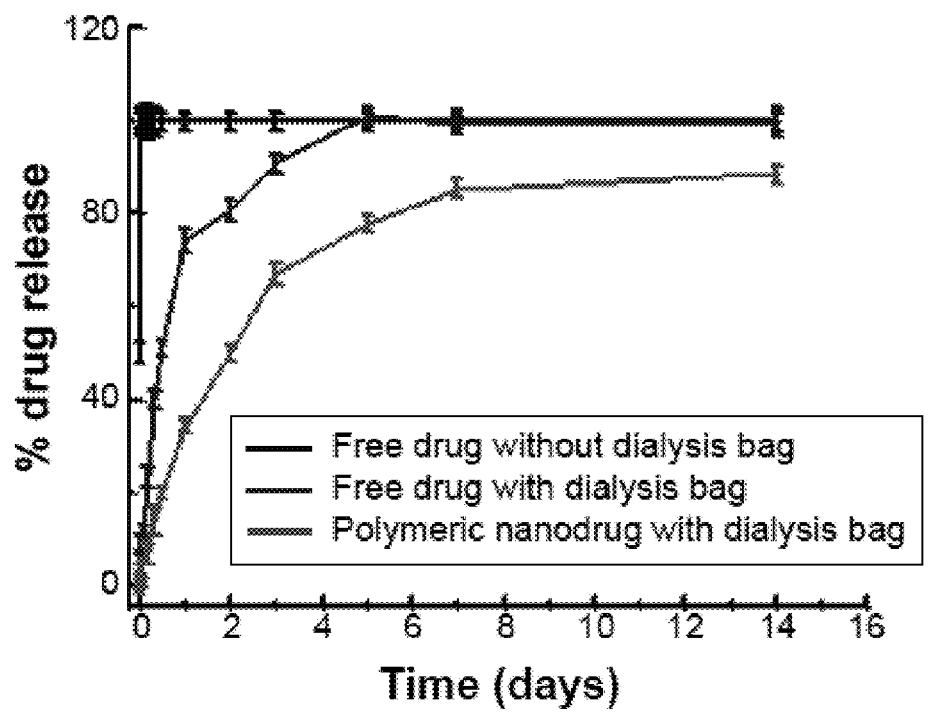

FIG. 4. Dissolution study of nanodrug in PBS in in vitro. Dispersion of the micelles in PBS (pH 7.4) placed in the dialysis bag and dialyzed against the respective buffer solution at 37° C. The released drug outside of dialysis bag were sampled at different time intervals (from 5 min up to 14 days) and measured by high performance liquid chromatography (HPLC). The data was expressed as 80% of drug released from the pluronics relatively to the initial drug loading.

Figure 5A:
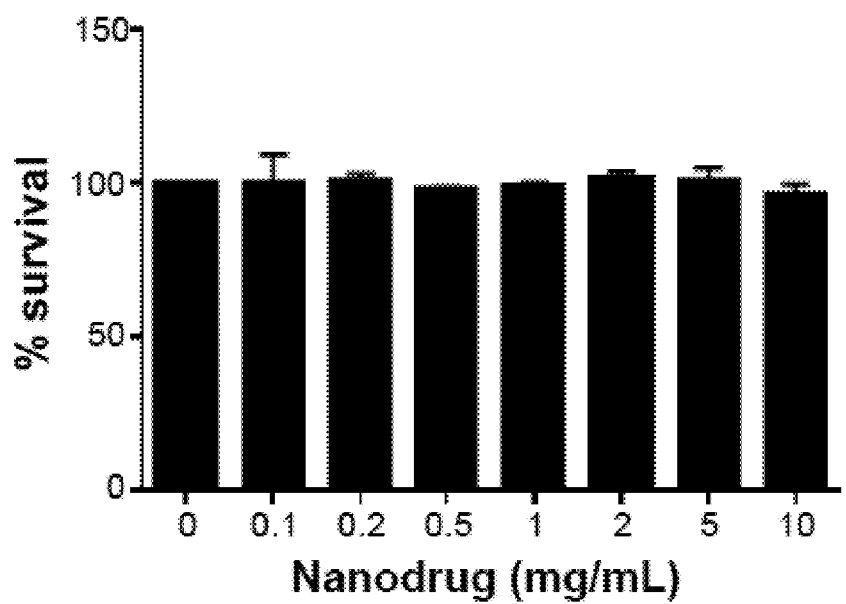
Figure 5B:
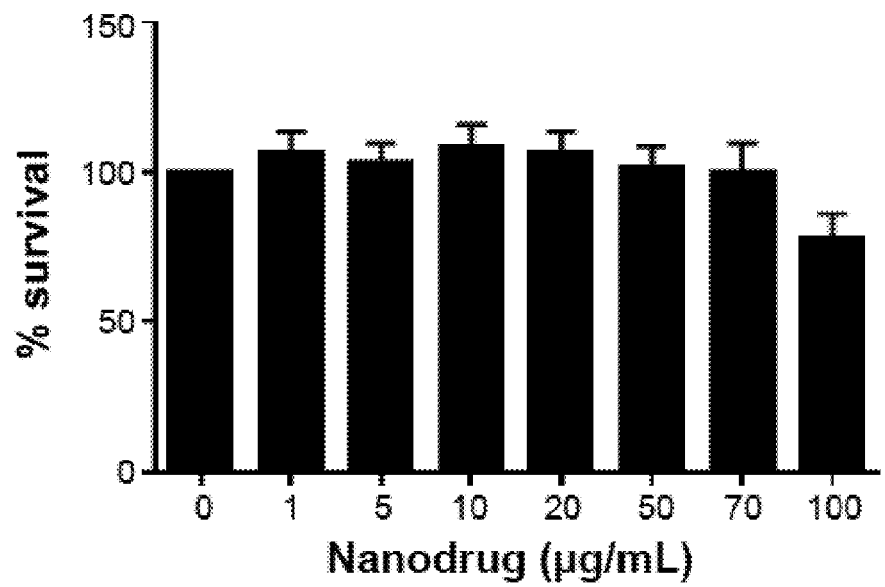

FIGS. 5A-5B. Cytotoxicity of nanodrug on Caco-2 cells and primary human macrophages. (5A) Caco-2 cells were exposed to 0.1-10 mg/ml concentration of nanodrug for 24 hrs. (5B) Primary human macrophages were exposed to nanodrug 1-100 μg/ml for 24 hrs, respectively. After incubation. MTS assay was performed and optical density of culture supernatant was measured at 490 nm. Data was presented as % survival of cells at different concentrations of nanodrug. Untreated cells were considered as control (0) with 100% viability. The changes in viability at different concentration of nanodrug compared to control found to be non-significant.

Figure 6:
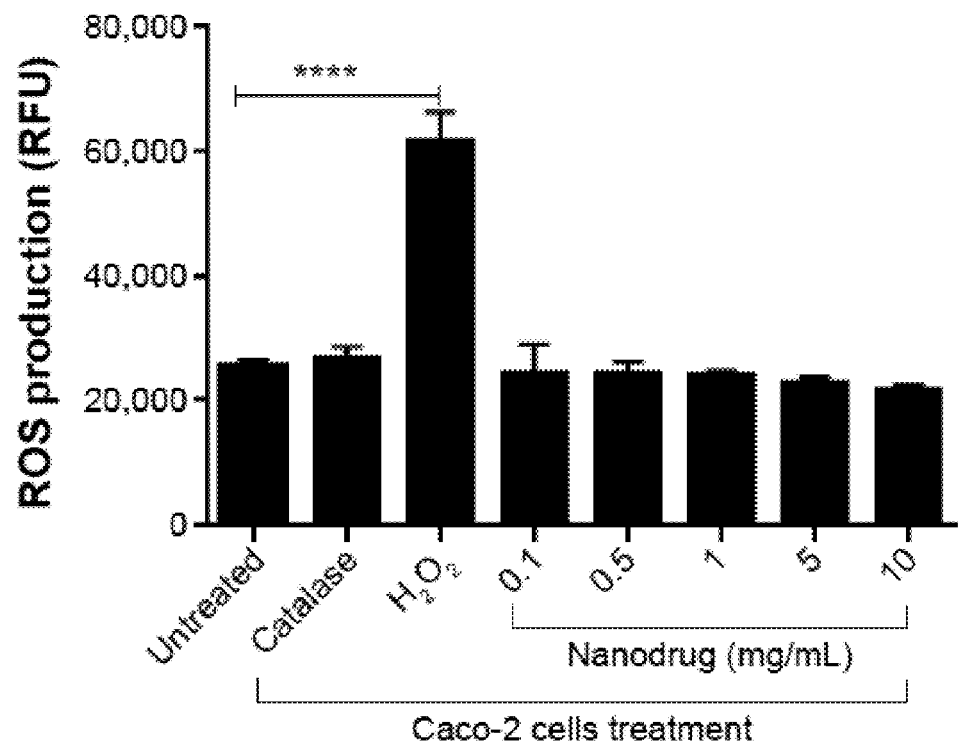
Figure 7A:
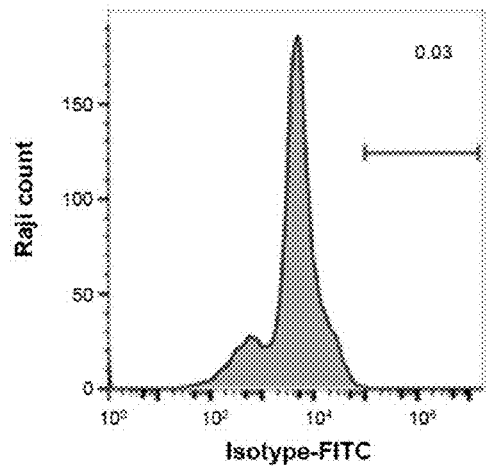
Figure 7B:
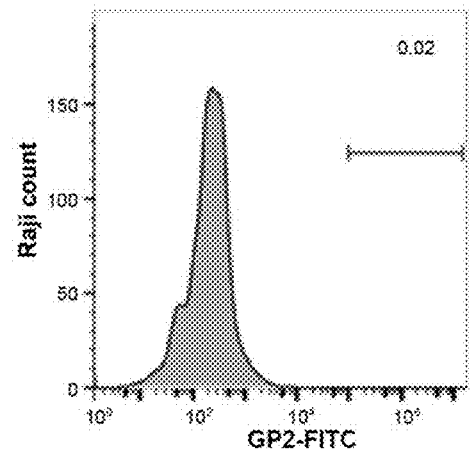
Figure 7C:
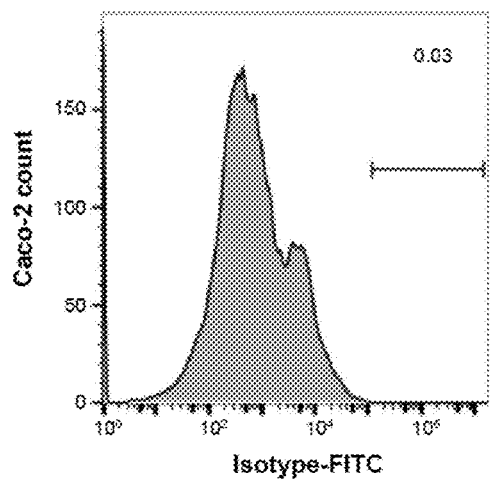
Figure 7D:
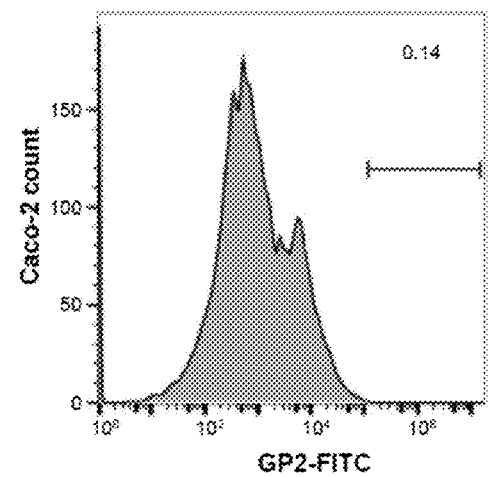
Figure 7E:
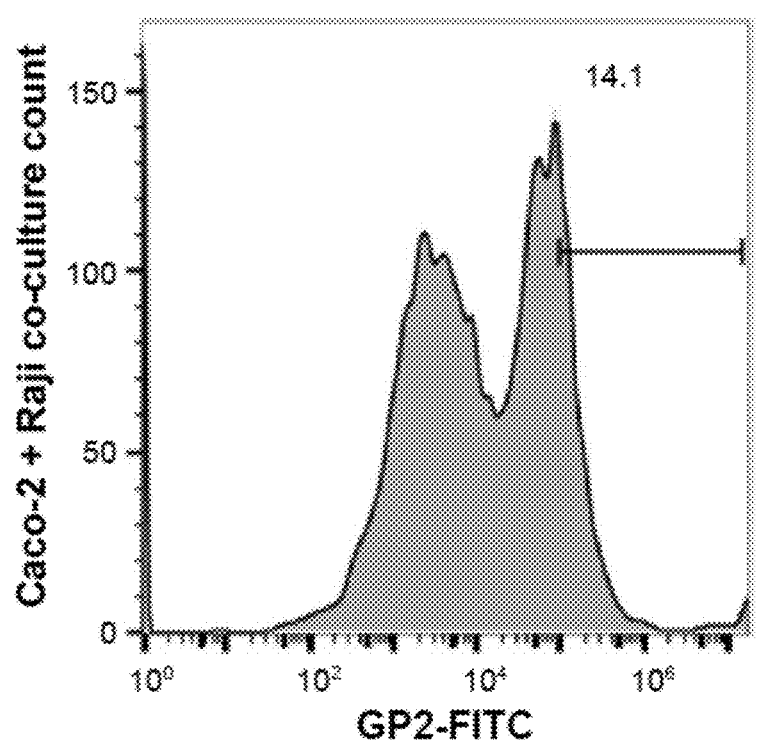

FIG. 6. Effect of nanodrug on reactive oxygen species (ROS) production in Caco-2 cells. Cells were exposed to 0.1-10 mg/ml concentrations of nanodrug for 24 hrs. At the end of incubation ROS assay was performed. The fluorescence was detected at 485 nm excitation and at 528 nm emission spectra. Catalase was used as antioxidant control and $H_2O_2$ was used as positive control. Data are expressed as mean±SE of relative fluorescence units (RFU) values of four independent experiments. A value of $p<0.0001$ was indicative of significance (****). There was no statistical significance between treated groups and control.

FIGS. 7A-7E. Flowcytometric analysis of M-cell like characteristics in Caco-2 and Raji cell co-culture system. Caco-2, Raji and Caco-2+Raji cells were cultured simultaneously and stained with anti-GP2 antibody at the end of the incubation. Cells were gated for GP2, based on isotype in respective cells.

Figure 8:
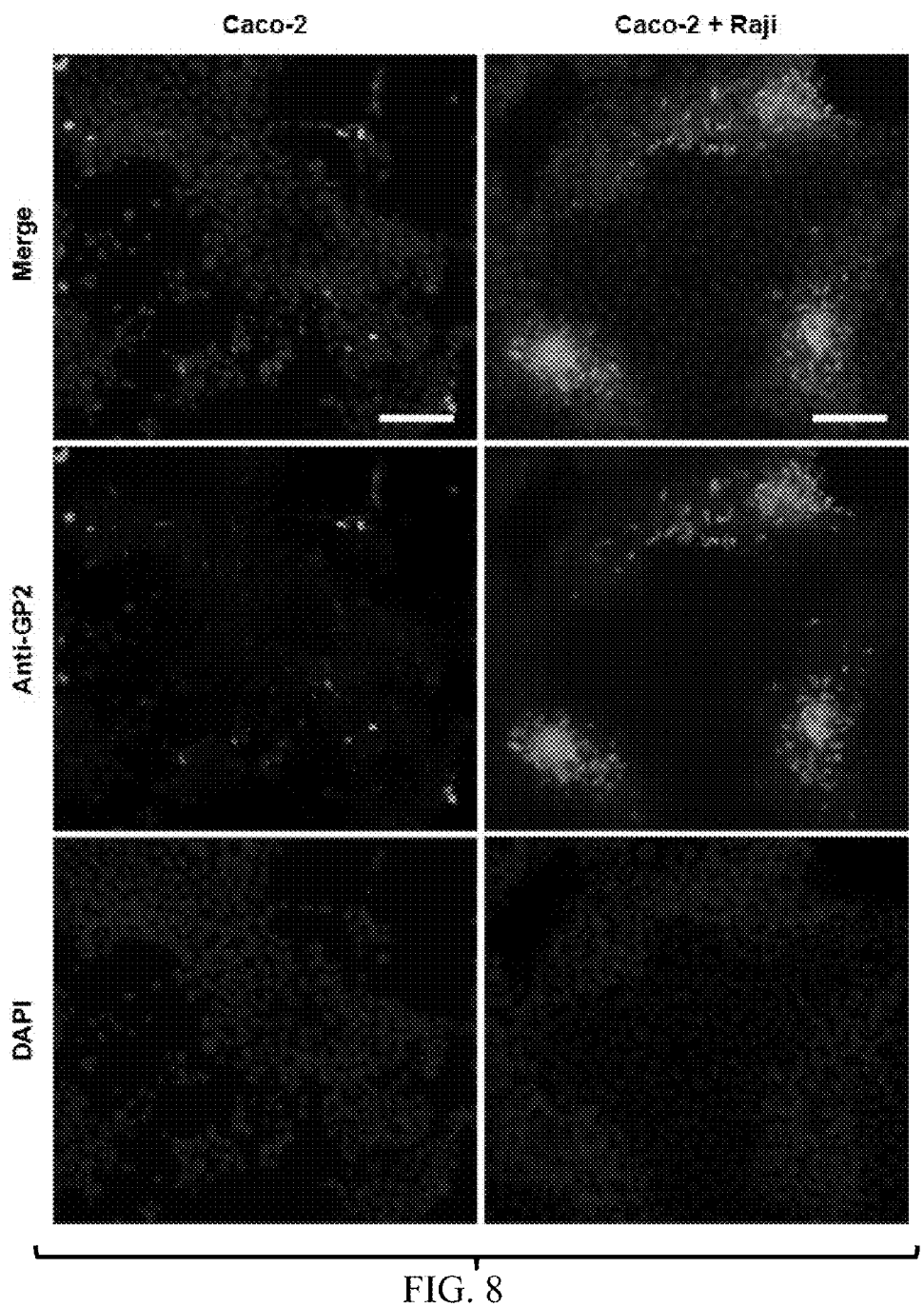

FIG. 8. Immunocytochemical analysis of M-cell characters in Caco-2 and Raji co-culture. Cells were exposed to anti-GP2 antibody after differentiation process and stained with fluorescent secondary antibody. Microscopic images were taken through Axio Imager 2. 4',6-diamidino-2-phenylindole (DAPI) (in blue) indicated the cell nucleus and the cells those have developed M-cell like characteristics were stained with GP2 antibody (green).

Figure 9A:
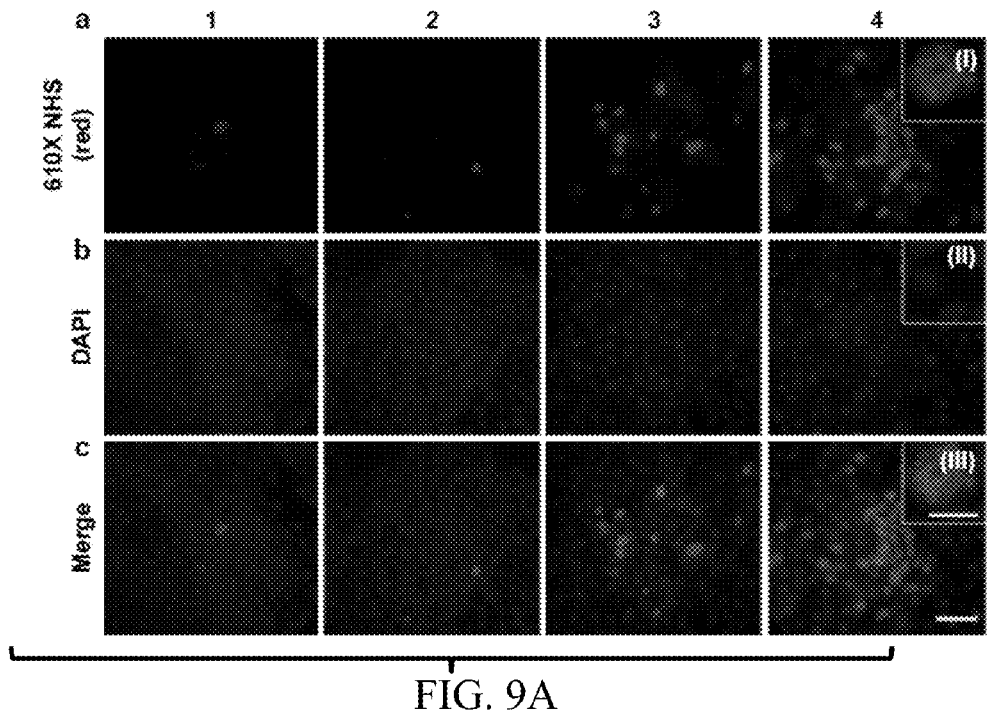
Figure 9B:
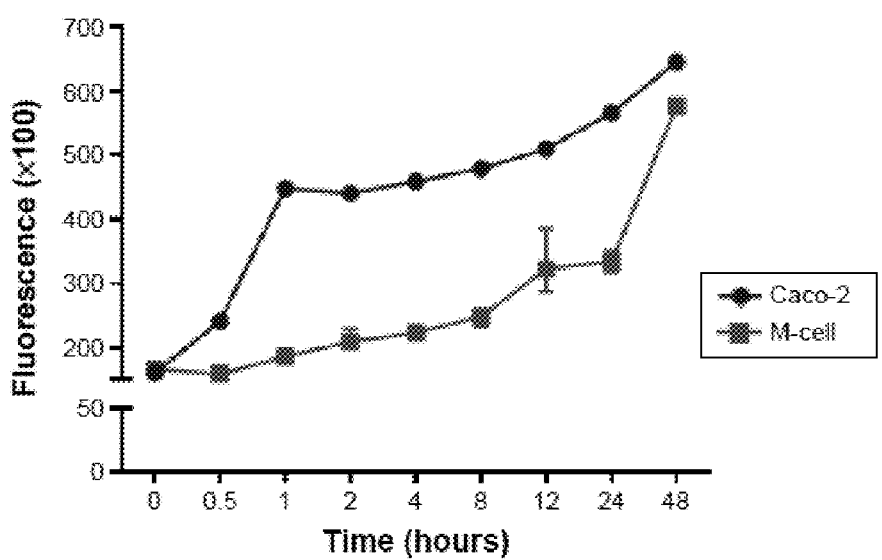

FIGS. 9A-9B. Uptake and release of fluorescent dye (NHX-610x) labelled nanodrug (FND) by M-cells. (9A) Uptake of anti GP2 conjugated nanodrug by M-cells within 2 hrs of incubation. Caco-2 and M-cells were treated with and without antibody (GP2) tagged with FND. The treatments were as follows (From left to right): (1) Caco-2 cells treated with FND, (2) Caco-2 cells treated with FND+GP2, (3) M-cell treated with only FND and (4) M-cell cells treated with FND+GP2. Cells were stained with DAPI in order to observe the localization of FND and represented in following order (A) FND, (B) DAPI and (C) FND and DAPI merged (scale bar 50 urn). Co-localization of FND on the cell surface was shown in magnified image in a (i), (ii) & (iii) (scale bar=20 urn). (9B) Release of FND in vitro trans-well co-culture model at lower chamber. Drug release was observed with respect to fluorescence measurement. Fluorescent drug release was significantly sustained in M-cell than Caco-2 cells ($p<0.0015$).

Figures 10A, 10B:
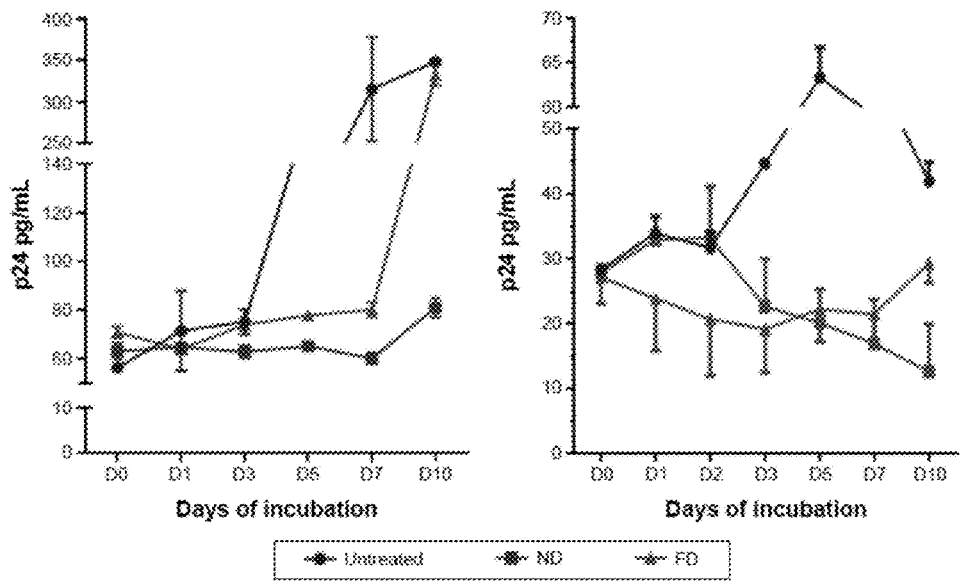
Figure 10C:
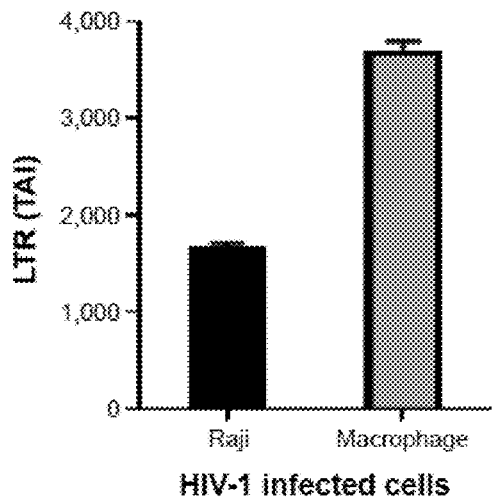

FIGS. 10A-10C. Comparative analysis of anti-HIV activity of nanodrug vs unformulated EFV on macrophages and M-cells. (10A) Effect of nanodrug on HIV infected macrophages compared to EFV. (10B) Effect of nanodrug or EFV was observed on HIV replication in M-cell culture model. HIV replication was monitored with respect to p24 protein level in the culture supernatant at different times (days). The data represented with respect to p24 level vs time (days) in untreated, nanodrug treated (ND, in green) and EFV drug (FD, in red) treated M-cells exposed to HIV ($p=0.001$). Untreated and HIV infected macrophage/Raji cells were treated as positive control (in blue). Statistical significance was calculated with respect to p values ($p=0.001$). (10C) HIV LTR R/U5 gene expression was done through PCR. The two columns show HIV infection in the Raji (black) and macrophages (gray) cells after 10 days of incubation. The long terminal repeat (LTR) gene expressions in both cells were expressed in Transcript Accumulation Index (TAI) and normalized with housekeeping gene GAPDH.

DETAILED DISCLOSURE

The present invention provides novel, long-acting nanoformulated drugs and targeted drug delivery methods, and uses thereof. In one embodiment, the nanoformulated drug is a retroviral drug.

In one embodiment, the nanoformulated composition comprises a nanocarrier with one or more incorporated drugs. The incorporated drug can be any drug. Specifically exemplified herein are drugs for treating retrovirus infections, including, for example, HIV. In an exemplary embodiment, the drug is efavirenz (EFV). In an exemplary embodiment the treatment is for a viral infection, which may be latent or active.

In one embodiment, the incorporated drug may be present in combination with other agents that are viral latency-activating drugs such as vorinostat, a histone deacetylase (HDAC) inhibitor and/or vaccine delivery agents In a further embodiment, the nanocarrier is associated with an agent for targeting microfold cells (M-cells). In a specific embodiment, the targeting agent binds to an M-cell marker known as glycoprotein 2 (GP2) or an alternative human M-cell specific antigen marker Sialyl Lewis A Antigen (SLAA). Via this mechanism, the nanodrug is targeted toward GALT.

In one embodiment, the nanocarrier is a poloxamer. Advantageously, in preferred embodiments the carrier prevents enzymatic digestion and facilitates the drug uptake at desired tissue and cells. In a specific embodiment, the poloxamer is a carboxylated Pluronic® block copolymer designated F127COOH.

In one embodiment, the nanoformulation is encapsulated in an enteric coated capsule. The nanocarrier and/or enteric coating can protect the formulation from stomach digestion and facilitate sustained release of the incorporated drug(s) in GALT where M-cells are present.

In one embodiment, the subject invention provides a system that facilitates directed targeting of drugs to an area within an animal body, preferably a human body, whereby the targeted area can be, for example, GALT.

In accordance with the present invention, the nanoformulated drug can be delivered to a mammal conveniently, e.g., by oral administration.

The terms "drug" and "active agent," as used in the present application, include any natural or synthetic substance that has a physiological effect when administered to an animal. As used herein, the terms "drug" and "active agent" include therapeutic agents, vaccine agents and diagnostic agents. The drug can be suitably employed in accordance with the invention with animals (subjects), particularly mammals including humans, veterinarian animals and farm animals.

In one embodiment, the method of the invention comprises the steps of preparing the nanodrug with at least one drug, administering the nanodrug to an animal in a manner that allows the drug to reach the target area, and allowing the drug to be released from the carrier to achieve the desired pharmacological effect in a sustained manner.

In one embodiment, the present invention provides a targeted nanodrug delivery system whereby an enteric coated capsule is administered orally. This nanodrug-containing capsule survives stomach digestion and enters the intestine. In the intestine the capsule is rupture due to the basic pH, and releases the nanodrug. Following release, the composition binds to, or otherwise associates with, an M-cells of the intestine. Once attached to the M-cells, the nanodrug is transferred from the intestine to GALT via transcytosis mechanisms.

Advantages of this invention include: (1) administration can be oral. By using an enteric coated capsule the composition can pass through to the intestine where a majority of HIV-infected lymphoid tissues are present, (2) by targeting M-cells it is possible for an anti-HIV drug to directly act on HIV in GALT, where traditional drugs cannot reach due to the fine structure of lymph nodes and stomach digestion and (3) the composition results in sustained release of the active agent.

Accordingly, this drug can be given orally once/twice a week instead of every day as with current therapy.

Poloxamer

An important characteristic of poloxamer solutions is their temperature dependent self-assembling and thermo-gelling behavior. Concentrated aqueous solutions of poloxamers are liquid at low temperature and form a gel at higher temperature in a reversible process. The transitions that occur in these systems depend on the polymer composition (e.g., molecular weight and hydrophilic/hydrophobic molar ratio).

Because the lengths of the polymer blocks can be customized, many different poloxamers exist that have slightly different properties. For the generic term "poloxamer," these copolymers are commonly named with the letter "P" (for poloxamer) followed by three digits: the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content).

For the Pluronic and Synperonic tradenames, coding of these copolymers starts with a letter to define its physical form at room temperature (L=liquid, P=paste, F=flake (solid)) followed by two or three digits, the first digit (two digits in a three-digit number) in the numerical designation, multiplied by 300, indicates the approximate molecular weight of the hydrophobe; and the last digit×10 gives the percentage polyoxyethylene content.

Targeting Entities

In a preferred embodiment, the composition comprises an entity that targets the composition, with the accompanying drug, to M-cells. The entity may be, for example, an antibody or antibody fragment. Specifically exemplified herein are antibodies to glycoprotein 2 (GP2), which is expressed at the surface of M-cells. Entities that target (e.g., bind with) other markers of M-cells can also be used in accordance with the subject invention. Preferably, the targeting entity is specific for M-cells.

"Specific," as employed herein, refers to an antibody, or other entity, that only recognizes the target to which it is specific or that has significantly higher binding affinity to the target to which it is specific compared to binding to molecules to which it is non-specific, for example at least 5, 6, 7, 8, 9, 10 times higher binding affinity.

Antibodies, including chimeric antibodies can be used according to the subject invention. Chimeric antibodies are those antibodies encoded by immunoglobulin genes that have been genetically engineered so that the light and heavy chain genes are composed of immunoglobulin gene segments belonging to different species. These chimeric antibodies can be less antigenic. Bivalent antibodies may be made by methods known in the art (Milstein et al, 1983, Nature 305:537-539; WO 93/08829, Traunecker et al, 1991, EMBO J. 10:3655-3659). Multi-valent antibodies may comprise multiple specificities or may be monospecific (see for example WO 92/22853).

In one embodiment the antibody for use in the present invention is humanised. As used herein, the term "humanised antibody molecule" refers to an antibody wherein the heavy and/or light chain contains one or more CDRs (including, if desired, one or more modified CDRs) from a donor antibody (e.g., a murine monoclonal antibody) grafted into a heavy and/or light chain variable region framework of an acceptor antibody (e.g. a human antibody) (see, e.g. U.S. Pat. No. 5,585,089; WO91/09967). For a review, see Vaughan et al, Nature Biotechnology, 16, 535-539, 1998.

The antibodies for use in the present invention can be purchased or they can be generated using various known methods, including phage display methods known in the art and including those disclosed by Brinkman et al. (in J. Immunol. Methods, 1995, 182: 41-50), Ames et al. (J. Immunol. Methods, 1995, 184:177-186); Kettleborough et al. (Eur. J. Immunol. 1994, 24:952-958), Persic et al. (Gene, 1997 187 9-18); Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. Techniques for the production of single chain antibodies, such as those described in U.S. Pat.

No. 4,946,778 can also be adapted. All of the references cited herein are incorporated herein, by reference, in their entireties. Also, transgenic mice, or other organisms, including other mammals, may be used to express humanized antibodies.

The antibody used in the present invention may comprise a complete antibody molecule having full length heavy and light chains or a fragment thereof and may be, but are not limited to, Fab, modified Fab, Fab', modified Fab', F(ab')$_2$, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing antibody fragments are well known in the art (see for example Velma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities e.g bispecific or may be monospecific (see for example WO 92/22853, WO05/113605, WO2009/040562 and WO2010/035012).

In one embodiment the antibody is provided as a fusion protein that comprises an immunoglobulin moiety, for example a Fab or Fab' fragment, and one or two single domain antibodies (dAb) linked directly or indirectly thereto, for example as described in WO2009/040562, WO2010/035012, WO2011/030107, WO2011/061492 and WO2011/086091 all incorporated herein by reference.

In one embodiment the fusion protein comprises two domain antibodies, for example as a variable heavy (VH) and variable light (VL) pairing, optionally linked by a disulphide bond.

In one embodiment the Fab or Fab' element of the fusion protein has the same or similar specificity as the single domain antibody or antibodies. In one embodiment the Fab or Fab' has a different specificity to the single domain antibody or antibodies, that is to say the fusion protein is multivalent. In one embodiment a multivalent fusion protein according to the present invention has an albumin binding site, for example a VH/VL pair therein provides an albumin binding site.

Antibody fragments and methods of producing them are well known in the art, see for example Verma et al, 1998, Journal of Immunological Methods, 216, 165-181. Particular examples of antibody fragments for use in the present invention are Fab' fragments which possess a native or a modified hinge region. A number of modified hinge regions have already been described, for example, in U.S. Pat. No. 5,677,425, WO99/15549, and WO98/25971 and these are incorporated herein by reference. Further examples of particular antibody fragments for use in the present invention include those described in international patent applications PCT/GB2004/002810, PCT/GB2004/002870 and PCT/GB2004/002871 (all filed on 1 Jul. 2004). In particular the modified antibody Fab fragments described in International patent application PCT/GB2004/002810 are preferred.

The antibody can be of any class (e.g., IgG, IgE, IgM, IgD and IgA) or subclass of immunoglobulin molecule. In one embodiment the antibody for use in the present invention is of IgG class and may be selected from any of the IgG subclasses IgG1, IgG2, IgG3 or IgG4.

The antibody for use in the present invention may include one or more mutations to alter the activity of the antibody. Angal et al (Angal, S., King, D. J., Bodmer, M. W., Turner, A., Lawson, A. D., Roberts, G., Pedley, B., and Adair, J. R. 1993.

Pharmaceutical Compositions

The nanoformulated composition drug delivery system of the subject invention can be delivered as part of a composition that further comprises a physiologically acceptable carrier and/or diluent allowing the transport of said composition to the target after administration.

The carrier and/or diluent can be any medium by which the desired purpose is achieved and which does not affect the capability of the nanoformulated composition to be directed to the desired target and to transport the drug(s) to this target for the desired pharmacological effect. Particularly, the carrier and/or diluent should not deteriorate the pharmacological potency of the drug and the capability of the delivery system to be directed to a desired target within the body.

In certain embodiments, the carrier and/or diluent is selected from water, physiologically acceptable aqueous solutions containing salts and/or buffers and any other solution acceptable for administration to a subject. Such carriers and diluents are well known to a person skilled in this field and include, for example, distilled water, deionized water, pure or ultrapure water, saline, phosphate-buffered saline (PBS), and solutions containing usual buffers which are compatible with the other components of the drug targeting system provided herein.

Enteric Coating

The macrophage or reticuloendothelial system (RES) can identify and clear foreign substances in both the blood and tissues. This aspect of the immune system brings obstacles for formulations applied by intravenous injection. Accordingly, in one embodiment, the subject invention combines an oral drug formula with nano-technique in which nanoparticle may escape from macrophage tracking because of an enteric coating.

The present in vitro data verified the stability of nanoparticles under intestine circumstance. Since the short period of drug release from nanodrug to the step of uptake by intestinal epithelium, this antibody digestion issue may be alleviated by our enteric coating capsule nano formulation. Because of the enteric capsule has the character of acid, the nanoformulation will come out from the cracked enteric capsule only at intestine site and achieve the targeted drug delivery to increase therapeutic efficacy.

The enteric (gastro-resistant) membrane material, e.g., polymer, can be one that will rupture in intestinal juices at a pH higher than that of the stomach, e.g., a pH of greater than 4.5, such as within the small intestine, and therefore permit release of the active substance in the regions of the small intestine and substantially not in the upper portion of the GI tract. In one embodiment, the enteric material begins to rupture in an aqueous solution at pH between about 4.5 to about 5.5. In another embodiment, the enteric material rapidly rupture in an aqueous solution at pH between of about 5. In another embodiment, the enteric material rapidly rupture in an aqueous solution at pH of about 5.5.

Preferably, the coating film will not undergo significant rupture until the dosage form has emptied from the stomach. The pH of the small intestine gradually increases from about 4.5 to about 6.5 in the duodenal bulb to about 7.2 in the distal portions of the small intestine (ileum). In order to provide predictable dissolution corresponding to the small intestine transit time of about 3 hours (e.g., 2-3 hours) and permit reproducible release therein, the membrane should begin to dissolve within the pH range of the duodenum, and continue to dissolve at the pH range within the small intestine.

Therefore, the amount (thickness) of enteric membrane should be sufficient to be substantially disrupted during the approximate three hour transit time within the small intestine (e.g., the proximal and mid-small intestine) and this coating film or membrane (such as thickness and types) can be adjustable from customer demand for specific therapeutic aims.

Enteric (gastro-resistant) materials can include, but are not limited to, one or more of the following: cross-linked polyvinyl pyrrolidone; non-cross linked polyvinylpyrrolidone; hydroxypropylmethyl cellulose phthalate, hydroxypropylmethyl cellulose acetate succinate, cellulose acetate succinate; cellulose acetate phthalate, hydroxypropylmethyl cellulose acetate succinate, cellulose acetate trimellitate; starch acetate phthalate; polyvinyl acetate phthalate; carboxymethyl cellulose; methyl cellulose phthalate; methyl cellulose succinate; methyl cellulose phthalate succinate; methyl cellulose phthalic acid half ester; ethyl cellulose succinate; carboxymethylamide; potassium methacrylatedivinylbenzene copolymer; polyvinylalcohols; polyoxyethyleneglycols; polyethylene glycol; sodium alginate; galactomannone; carboxypolymethylene; sodium carboxymethyl starch; copolymers of acrylic acid and/or methacrylic acid with a monomer selected from the following: methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate, or octadecyl acrylate, e.g. EUDRAGIT-L and -S series, including L 100-55, L 30 D-55, L 100, S 100, L 12.5, and S 12.5, available from Evonik Industries; polyvinyl acetate; fats; oils; waxes; fatty alcohols; shellac; zein; gluten; ethylacrylate-maleic acid anhydride copolymer; maleic acid anhydride-vinyl methyl ether copolymer; styrol-maleic acid copolymer; 2-ethyl-hexylacrylate maleic acid anhydride; crotonic acid-vinyl acetate copolymer; glutaminic acid/glutamic acid ester copolymer; carboxymethylethylcellulose glycerol monooctanoate; polyarginine; poly(ethylene); poly(propylene); poly(ethylene oxide); poly(ethylene terephthalate); poly(vinyl isobutyl ether); poly(vinyl chloride); and polyurethane. A combination of enteric materials may also be used. In one embodiment, the enteric material rapidly dissolves at pH 5.5 and higher, to provide fast dissolution in the upper bowel. For example, the enteric material can be selected from a copolymer of methacrylic acid and methyl methacrylate, and a copolymer of methacrylic acid and ethyl acrylate. For example, an enteric polymer is poly(methacrylic acid co-ethyl acrylate) 1:1 (EUDRAGIT L 30 D-55 and EUDRAGIT L100-55).

Examples of some enteric coatings are disclosed in U.S. Pat. No. 5,225,202, including beeswax and glyceryl monostearate; beeswax, shellac and cellulose; and cetyl alcohol, mastic and shellac, as well as shellac and stearic acid (U.S. Pat. No. 2,809,918); polyvinyl acetate and ethyl cellulose (U.S. Pat. No. 3,835,221); and neutral copolymer of polymethacrylic acid esters (Eudragit L30D) (F. W. Goodhart et al., Pharm. Tech., pp. 64-71, April 1984); copolymers of methacrylic acid and methacrylic acid methylester (Eudragits), or a neutral copolymer of polymethacrylic acid esters containing metallic stearates (Mehta et al., U.S. Pat. Nos. 4,728,512 and 4,794,001). Enteric coatings are also described in U.S. Pat. No. 9,233,077. All of these patents, and specifically their teachings with regard to enteric coatings, are incorporated herein, by reference, in their entireties. Such coatings comprise mixtures of fats and fatty acids, shellac and shellac derivatives and the cellulose acid phthlates, e.g., those having a free carboxyl content. See also Remington's Pharmaceutical Sciences, A. Osol, ed., Mack Pub. Co., Easton, Pa. (16th ed. 1980) at pages 1590-1593, and Zeitova et al. (U.S. Pat. No. 4,432,966), for descriptions of suitable enteric coating compositions.

One or more plasticizers can be added to enteric polymers in order to increase their pliability and reduce brittleness, as it is known in the art. Suitable plasticizers are known in the art and include, for example, butyl citrates, triethyl citrate, diethyl phthalate, dibutyl sebacate, PEGs (e.g. PEG 6000), acetyl triethyl citrate, and triacetin. In one type of embodiment, the plasticizer is triethyl citrate. While some enteric materials are flexible and do not require addition of plasticizers, more brittle polymers (e.g., Eudragit L/S types, Eudragit RL/RS, and Eudragit FS 30 D) benefit from plasticizers, e.g. in the range of 5 wt. % to 30 wt. % based on the dry polymer mass, e.g. about 8 wt. % to about 12 wt. % triethyl citrate with poly(methacrylic acid co-ethyl acrylate) 1:1.

The enteric membrane can be formed by any suitable process. Coating processes include pan coating, fluid bed coating, and dry coating (e.g., heat dry coating and electrostatic dry coating), for example. Pan coating and fluid bed coating using solvent are well established processes. In liquid coating, the enteric material and optional excipients (e.g. pigments, plasticizers, anti-tacking agents) are mixed in an organic solvent or water to form a solution or dispersion. The coating solution or dispersion is sprayed into solid dosage forms in a pan coater or a fluid bed dryer and dried by hot air. For example, in a Wurster fluid bed coating process, the coating fluid is sprayed from the bottom of the fluid bed apparatus, whereas in an alternative the coating fluid is applied by top spraying, and in another alternative tangential spray is applied.

The amount of enteric material applied is sufficient to achieve desired acid resistance and release characteristics. For example, in one embodiment the amount of enteric membrane will be sufficient to meet United States Phamacopeia (USP)<711> requirements (USP 36-NF 31) for delayed-release dosage forms, thereby not releasing 10.0 wt. % of drug after 2 hours in 0.1N HCl. In another aspect, the formulation will be sufficient to release at least 80% of the active in 20 minutes in pH 6.8 buffer solution, e.g. using the dissolution method of USP 36-NF 31 section <711>.

In one type of embodiment, the enteric membrane is present in an amount in a range of about 20% to 40%, or 25% to about 35% as measured by the weight gain compared to the uncoated particle cores, or in a range of about 25% to about 31% weight gain, or about 27% to about 31% weight gain, or about 28.5% to about 31% weight gain, based on the weight of the uncoated particle cores.

Delivering the Nanodrug to M-Cells

The epithelium layer that lies in the gut, except Peyer's patches, which contain M-cells, is impermeable to macromolecules including drug molecules. In the development of the subject invention, an in vitro culture system was adopted that reproduced the characteristics of M-cells. Because this in vitro model is the only tool to study the human M-cells, it was characterized in detail. The biological characterization revealed that the presence of Raji cells in co-culture with a monolayer of Caco-2 cells help the Caco-2 cells develop M-cell like characteristics. In order to confirm that, flow cytometric analysis was done with Caco-2 cells and Caco-2+Raji cells co-culture, respectively. The analysis indicated that there was significant change in the Caco-2 cell surface, which more closely resembles M-cells.

These data were also corroborated with other immunocytochemistry analyses indicating that the co-cultured cells have expressed M-cell specific characteristics confirming establishment of the in vitro M-cell model.

In order to observe the functional activity of the M-cell, anti GP2 conjugated fluorescent nanodrug (FND) was introduced in the M-cell model. Further, an M-cell mediated uptake and release study was performed to observe the uptake and release of nanodrug. The initial immunofluorescence study indicated that FND was taken up within the first 2 hrs of incubation. The FND+GP2 showed higher uptake, indicating the M-cell specific binding of anti-GP2 antibodies and adsorption of nanodrug. The absorption of FND, transport of FND by M-cells was observed at the lower chamber over a period of 48 hrs.

The fluorescence release study indicated that these cells provided sustained release of the nanodrug that was sustainable than unformulated drug. The mechanism of accumulation and release of unformulated drug and nanoformulated drug may be different. In particular, nanoparticles should enter by endocytosis-mediated transport and be released through recycling. This is a slow process compared to trafficking of the free low molecular weight drug. This sustained release process of the nanodrug of the current invention is particularly advantageous compared to the unformulated drug.

Treatment of Viral Infections, Including HIV

In a specific embodiment, the subject drug delivery system can be used to treat viral infections, including HIV. The antiretroviral drug may be selected from, for example, nucleoside reverse transcriptase inhibitors (NRTIs), non-nucleoside reverse transcriptase inhibitors (NNRTIs), nucleotide analog reverse transcriptase inhibitors (NtARTIs or NtRTIs), protease inhibitors (PIs), and integrase strand transfer inhibitors (INSTIs). In certain embodiments a viral latency-activating drug can be used. The viral latency-activating drug may be selected from, for example, protein kinase C (PKC) agonists, histone deacetylase (HDAC) inhibitors, and nuclear factor kappa-light-chain-enhancer of activated B cells (NF-κB).

In an exemplary embodiment, a combination of tenofovir (teno), an NRTI, and vorinostat (vor), an HDAC inhibitor, can be used.

Advantageously, technologies provided herein may also be applied to other combinations of antiretroviral drugs including, but not limited to, nucleotide reverse transcriptase inhibitor+nucleotide reverse transcriptase inhibitor+protease inhibitor, and nucleotide reverse transcriptase inhibitor+protease inhibitor+integrase inhibitor. Further, in other embodiments, the drug delivery system can also be used to treat other types of viral infections using specific drug or drug combinations.

Latency-breaking and antiviral efficacy of the drug delivery system provided for treating IIIV can be determined via, for example, quantification of p24 antigen in a primary human astrocytes (HA) infection model, similar to what was described by Nair et al. (Nair M, Guduru R, Liang P, Hong J, Sagar V, Khizroev S. Externally controlled on-demand release of anti-HIV drug using magneto-electric nanoparticles as carriers. *Nat Commun.* 2013; 4:1707).

The drug release profile of an exemplary formulation, e.g., the {MNPs+(teno+DS)$_2$+vor} formulation, can be determined via an in vitro pharmacokinetic study in PBS (pH=7.4). As with the measurements of zeta potential, release profile of uncoated, 1BL-coated, and 2BL-coated drug particles, respectively, can be compared to demonstrate improved drug release profile. Other vaccines can also be administered orally via this mechanism.

Overall, the data indicate the ability of M-cell to carry anti-HIV drug from gut side to the GALT side. In this regard, the binding of anti-GP2 antibodies improves targeting of the drug molecule towards M-cells and the transmigration capability of the M-cells to take the drug molecule to the other side of the barrier.

The anti-HIV activity data indicated that treatment of cells with free drug or nanodrug significantly lowered levels of viral replication compared to untreated Raji cells. In the case of free EFV there was an immediate decrease in viral replication as expected; however, rebound of viral p24 level within day ten indicated failure of sustained inhibition of HIV replication in in vitro. Whereas, in case of the nanodrug of the current invention, the immediate response was slower but the subsequent sustained inhibition of viral replication was observed with consistent decline of p24 viral protein even on day 10 post infection.

In accordance with the subject invention, an anti-HIV drug molecule transmigrates through M-cells and then releases anti-HIV activity. Advantageously, the current invention can be used to reduce the viral reservoir in the GALT compared to unformulated drug.

In accordance with the subject invention, M-cells can be used to translocate particles from intestine to lymphoid system. By utilizing this system, the F127COOH-EFV, for example, formulation can be used for highly efficient targeted drug delivery system to the GALT. The steady release of nanodrug is also advantageous compared to free drug. The invention can be used to significantly reduce the viral load of the GALT and improve the treatment outcome.

Materials and Methods

Synthesis of Carboxylated Functional Pluronic F127 (F127COOH)

Figure 1A:
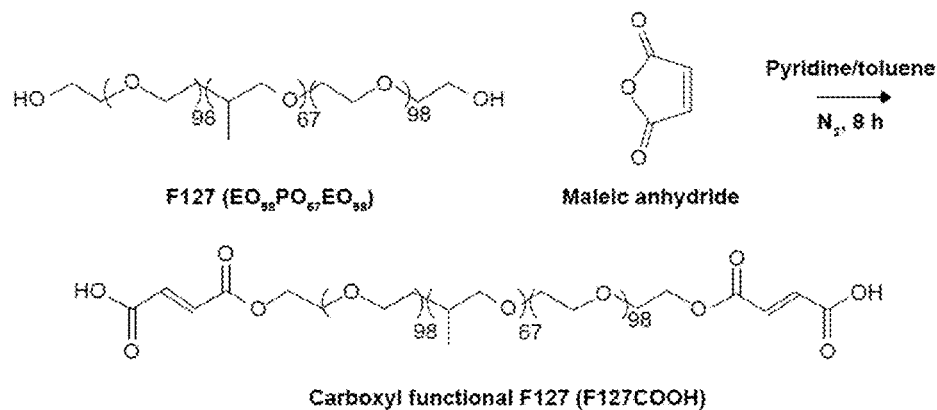
FIGS. 1A-1B. (1A) shows the illustration of synthetic routine of carboxyl functionalized triblock copolymer F127

As shown in FIG. 1A, carboxylated ABA triblock copolymer F127 (F127COOH) was synthesized according to the literature with minor modification[17]. Briefly, maleic anhydride (1.93 g, 19.5 mmol) was added to a solution of F127 (25.0 g, 1.95 mM) in a mixed solvent of toluene (100 mL) and pyridine (5 mL). The whole mixture was stirred for 8 h at room temperature (RT) under a nitrogen stream. After purification by precipitation from excessive diethyl ether thrice, 21.3 g (85%) of F127COOH as a light brown solid was obtained. The preparation of drug loaded Pluronics with antibody conjugation (F127-COOH-EFV-GP2)

In a typical experiment, hydrophobic EFV dissolved in chloroform (2.0 mg) was mixed with F127COOH in chloroform (20 mg) at a weight ratio of 1:10. The mixture was gently stirred for 5 min and a rotary vacuum evaporator with a water bath of 35° C. was applied to evaporate the organic solvent. The deposited film on the vials was hydrated with 1.0 ml of HPLC water. The resulting clear dispersion was kept at RT for further use.

The 200 μl of F127COOH-EFV aqueous solution obtained in the previous step was incubated with 20 μl of EDC solution (1.92 mg/mL in water, $1.04 \times 10^{-6}$ mol) for 5-10 min, and then 14 μl solution of anti-GP2 antibodies (0.5 mg/ml, $4.67 \times 10^{-11}$ mol) was added[18]. After 1.5 h of incubation, the antibodies conjugated F127COOH-EFV nanoparticles spun down at 10,000 rpm for 10 minutes, and then re-dispersed in 220 μl of PBS for further application.

Transmission Electron Microscopy (TEM)

The size of the F127COOH-EFV micelles was determined using negative staining technique of transmission electron microscopy. In brief, one drop of F127COOH-EFV micelles was spread on carbon support film on 400 mesh Cu grids (type B, Ted Pella, USA). The grid samples were examined using TEM imaging as explained earlier. The samples on the grids were negatively stained with phosphotungstic acid (2.0% w/v; pH 6.4) and dried at RT.

Particle Size and Zeta Potential

The hydrodynamic radius, size distribution, and surface charge measurements of F127COOH-EFV were carried out at 25° C. in dynamic laser scattering (DLS) (90 Plus particle size analyzer, Brookhaven Instruments, Holtsville, N.Y., USA). Scattered light was detected at a 90° angle and a temperature of 25° C. Hydrodynamic size was expressed as mean±SEM of triplicate measurements. The aggregation stability of the nanoparticles in 10 mM phosphate buffer was examined over 25 days.

Colloid and Physiological Stability

The nanocarriers were stored at 4° C. and the durability of their structural integrity was evaluated by measuring their size for up to 28 days. Further, their stability in blood fluid was assessed by measuring their size in an in vitro closed circulatory system at 37° C. for up to 28 h. This closed circulation system was set up using a bidirectional, self-priming peristaltic pump (Mini Pump Peristaltic Pump Variable Flow C-2 Lab Pump, Fisher Scientific, Boston, Mass., USA). The nanoformulation was allowed to circulate in a 0.8 mm capillary 120 times at a flow rate of 1 ml/min. The circulating medium was prepared with 5% dextran-500 (catalog no 50-247-495, Thermo Fisher Scientific, Boston, Mass., USA) in PBS, which gave a viscosity equivalent to that of blood (4.5 cP). Samples were collected after 10, 30, 60, and 120 circulations and subjected to size analysis by DLS[19].

Dissolution of the Nanoformulation

A 2 ml solution of F127COOH-EFV nanoparticles (0.5 ml, concentration: 2 mg/20 mg ratio drug/F127COOH) was placed into dialysis bag (molecular cutoff: 6 kDa), sealed, and put into a tube filled with 30 ml dissolution solution (composition: 0.1% Tween 20 aqueous solution). The tube was placed on a shaker with 37° C. at 150 rpm. At each time point (0, 5, 10, 15, 30, 60 min, 2, 4, 8 hrs, 1, 2, 4, 6, 8, 10, 12 and 14 days), 100 µl of solution was taken out from the tank where drug was releasing out of the dialysis bag and 100 µl of fresh dissolution was re-filled. The same concentration of free drug was used as a control.

At the last time point, the drug concentration was determined by HPLC (150 mm×4.6 mm column, injection volume: 20 µl, detection wavelength: 215 nm, temperature of performance: 30° C., retention time: 19.827 min).

In Vitro M-Cell Co-Culture Model

The Caco-2 cells were cultured in DMEM (Gibco, USA) with 10% v/v FBS and Raji cells were cultured in RPMI 1640 medium supplemented with 10% (v/v)+1% Penicillin and Streptomycin solution. The in vitro M-cell co-culture model was adopted from previous studies[11,13].

Briefly, 0.1 and 1.5 ml DMEM complete media were added to the apical and basolateral sides of the 24 well trans-well plate, respectively. The Caco-2 cells (5×10$^5$ cells/well) were seeded on the apical sides of the trans-well and medium of the apical side was changed every other day for next 14 days of culture. Raji cells (3×10$^5$ cells/well) were suspended in complete RPMI 1640/DMEM (1:2) mixture then added to the basolateral chamber of the transwell, and co-culture was maintained for 12 days. The integrity of the epithelial barrier was measured by transendothelial electrical resistance (TEER) using Mil licell ERS microelectrodes (Millipore, City, USA)[20]. Caco-2 cells were also cultured without Raji cells to serve as a control.

Flow Cytometry

M-cells or differentiated Caco-2 cells were scrapped out of the trans-well culture and washed with PBS. M-cells were further washed with Flow cytometry (FACS) buffer (PBS, 0.5-1% BSA or 5-10% FBS, 0.1% NaN3 sodium azide) and probed with the anti-GP2 antibodies (2 ug/ml MBL, Japan) and incubated at RT for 20 min in the dark. Cells were then washed with the FACS buffer to remove the unbound antibodies and fixed with 2% paraformaldehyde and analyzed by FACS (Acuri C6, BD bioscience, Franklin Lakes, N.J., USA). Caco-2 and Raji cells were gated for GP2 based on the isotype gating on respective cells.

Immunofluorescence Staining of M-Cells

Caco-2 cells cultured on coverslip were added to Raji cells seeded in transwell culture plate. After the incubation, the Caco-2 monolayer was washed several times with PBS and fixed with 4% paraformaldehyde for 30 min at 4° C. The cells were washed with 0.1% Triton X-100 in PBS for 3 times for 5 min each. Primary antibodies (antiGP2 antibodies 2.5 ug/ml) were added in PBS with 0.1% Triton X for 1 hr. The cells were washed 3 times with 0.1% Triton X-100 in PBS for 5 min. After washing, secondary antibodies (Alexa Fluor 488 goat anti mouse antibodies, 10 ug/ml) were added and incubated at RT for 45 min. Cells were washed again with 0.1% Triton X-100 in PBS. Cover-slips were mounted on the slides with Prolong®Gold antifade reagent (Invitrogen, Carlsbad, Calif., USA) before proceeding for confocal microscopy.

The stained cells were examined using DeltaVision Imaging System (DV Elite™ System; Applied Precision, Mississauga, Canada) and observed with 60× oil immersion objectives. Cellular Uptake of Fluorescent Nanodrug (FND)

To examine the M-cell mediated drug transport in the in vitro system, a specially designed nanoformulation was prepared. For this purpose, F127-COOH-EFV-GP2 was further conjugated with fluorescent dye Alexa Fluor 610x-NHS ester (Invitrogen, Grand Island, N.Y., USA)[21] before the experiment. The uptake of FND by M-cells was investigated using a laser scanning microscope (Axio Imager 2, Carl Zeiss, Germany).

The ethanol treated glass slides were put in 6-well plates and coated by 0.01% poly-L-Lysine. The Caco-2 cells were seeded in these 6-well plates at the density of 5×10$^5$ cells/well and allowed to adhere and grow. In one set of wells Caco-2 cells were co-cultured with Raji cells for 5-7 days to obtain M-cells and other set of cells were kept as control.

At the end of the incubation, cells were washed and supplemented with fresh media containing 0.07 mg/ml of nanodrug and incubated at 37° C. for 2 hrs. After the incubation, cells were washed with PBS to remove any unabsorbed free nanodrug. Fluorescence was measured in the lower (receiving) chamber from 0 hr-48 hrs in order to observe the FND transport via M-cells. For the confocal imaging studies, the cells were fixed with paraformaldehyde for 30 min, mounted on the slide, and images of M-cells with accumulated FND were obtained as describe above.

Cellular Toxicity of Nanodrug

Cytotoxicity of the nanoformulation was determined by using MTS assay (G3582, Promega, Madison, Wis., USA,) on Caco-2 cells and primary human macrophages.

Briefly, cells were pre-incubated in 96-well plates with Caco-2 cells and then treated with various concentrations of nanodrug (0.1 to 10 mg/ml) for 24 h at 37° C. In case of primary human macrophages, cells were exposed at the concentrations of 1-100 ug/ml of nanodrug for 24 hrs, separately. After the treatment, cells were washed and incubated with fresh respective growth medium. Cells were further incubated with 20 µl of MTS reagent (CellTiter 96® AQueous One Solution, Madison, Wis., USA) in complete 100 µl cell media for 1 hr at 37° C.

After the incubation, the absorbance at 490 nm was measured using the BioTek plate reader (BioTek, Winooski, Vt., USA). Untreated cells incubated with fresh media alone were considered as a control. All measurements were taken eight times.

The net absorbance (A) was taken as index of cell viability. The cell viability was calculated as sample/control×100%. The nanoformulations that did not cause more than 10% loss in cell viability after at least 24 hours exposure were considered nontoxic.

Reactive Oxygen Species (ROS) Assay

ROS productions following exposure of different concentrations of nanodrug (0.1 to 10 mg/ml) were detected in Caco-2 cells using dichlorofluorescein diacetate assay (DCF-DA; Molecular Probes, Eugene, Oreg.) as per previous published protocol[22]. Cells were cultured in 96-well plates (100,000 cells/well) overnight to allow 70% confluence. The next day, cells were treated with different concentrations of nanodrug for 24 hrs as mentioned above. The following day, cells were washed and pretreated with anti-oxidant, catalase (0.001 mg) for 2 hours. Next, the cells were treated with DCF-DA (100 uM) for 1 hr at 37.0 and finally read in a BioTek Synergy HT microplate reader (excitation 485 nm and emission 528 nm; BioTek, Winooski, Vt.). Cells treated with $H_2O_2$ (50 uM) for 2 hours was considered as positive control[22].

Anti-HIV Activity of Nanodrug

The nanodrug was further investigated for anti-HIV activity in primary human macrophage and M-cell culture model, respectively.

Human peripheral blood mononuclear cells (PBMC) were isolated from healthy donor and differentiated to macrophages as per previously published protocol[23]. Briefly, PBMC were isolated with Ficoll-Hypaque (Pharmacia) gradient and cells were allowed to differentiate for 7 days in the presence of human macrophage colony stimulating factor (MCSF, Sigma) to macrophages. Following 7 days of incubation, macrophages were infected with HIV-1 1Ba-L (NIH AIDS research and reference reagent program. Cat#510) (100 ng/ml) and incubated for 24 hrs. The next day, cells were thoroughly washed to get rid of any unattached virus particle and fresh media was added. At the same time, same concentration (70 ug/ml) of nanodrug and unformulated drug (EFV) were added to these cells separately. The HIV infected macrophages were served as control.

The nanodrug/EFV drug treated cells were monitored for up to 10 days along with infected control cells. The cell supernatant was collected at day 0, 1, 3, 5, 7 and 10 days post treatment. The viral p24 level in the supernatant was measured with p24 ELISA assay (Cat. #0801200, Zeptometrix, USA). The minimum assay detection limit for p24 antigen by ELISA was 7.8 pg/ml as provided by the manufacturer. The p24 level at different time points gave the level of viral inhibition with nanodrug and EFV. The p24 level of the culture supernatant was inversely proportional to Anti-HIV activity of nanodrug.

Simultaneously, a parallel anti-HIV activity study was set up in an in vitro model of M-cell. In this model, Raji cells were exposed with HIV-1Ba-L at the concentration of (100 ng/ml) for 24 hrs in a co-culture and then washed from unattached viral particles[24,25]. Following that, same concentration (70 ug/ml) of nanodrug and EFV were added to M-cell culture model separately. The M-cell co-culture model was observed for ten days for viral replication which was measured by p24 ELISA assay (Zeptometrix, USA) at different time points up to 10 days. The untreated Raji cells were kept as a control for all the experiments related to drug activity. In the M-cell culture model, infected Raji cells were also treated with EFV to compare with nanodrug. The effect of nanodrug on HIV replication was measured for up to 10 days post treatment in culture supernatant.

At the end of both the experiments, a quantitative HIV-1 DNA protocol (LTR real-time PCR) was used to analyze the viral transcripts in HIV infected Raji cells and macrophages. This was done in order to ensure that untreated macrophages and Raji cells got infected with the exposure of HIV-1 (100 ng/ml). The following previously published[23] primers and probes were used: LTR U5/R-sense-5'-GGCTAACTAGGGAACCCACTG-3' and antisense-5'-CTGCTAGAGATTTTCCACACTGAC-3', probe 5'-FAM-TGTGTGCCCGTCTGTTGTGTG-TAMRA-3'. Relative gene expression was quantitated and the mean fold change in expression of the target gene was calculated using the comparative CT method (Transcript Accumulation Index (TAI)=2-ΔΔCT). All data were normalized for quantity of RNA input by performing measurements on an endogenous reference gene, GAPDH.

Statistical Analysis

All experiments were performed in replicates and data are presented as mean±SE. The statistical analysis was done by two-tailed paired t-test with GraphPad Prism software (GraphPad Prism software Inc. San Diego, Calif.). A p value of <0.05 was considered as significant.

EXAMPLES

Example 1—Preparation and Characterization of a Nanodrug Formulation

Figure 1B:
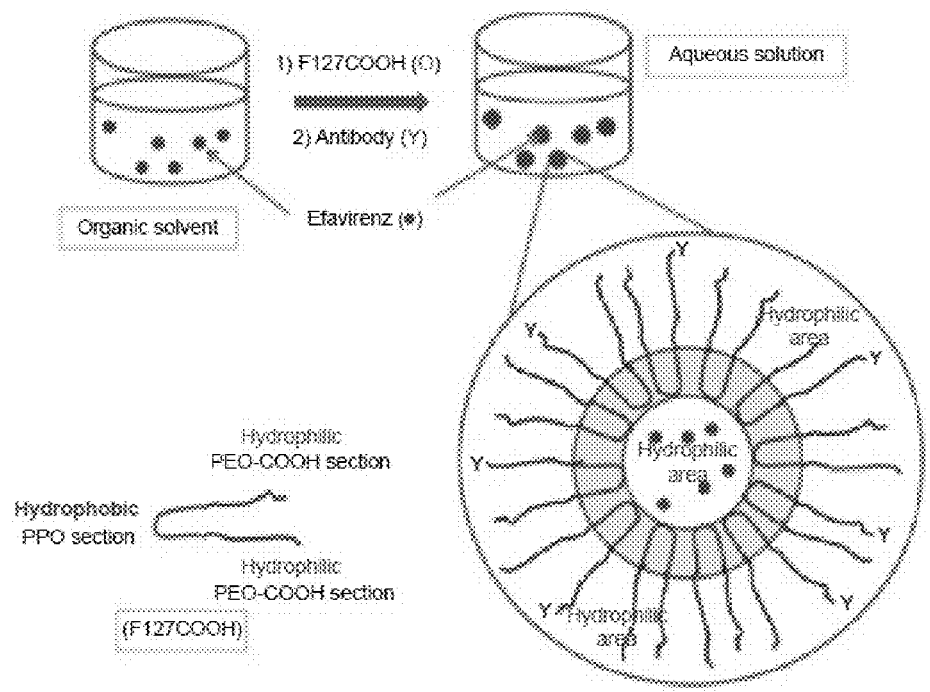

FIGS. 1A-1B show an example of a F127COOH-EFV nanodrug formulation preparation according to the current invention. The synthetic yield of the F127COOH from F127 was around 85%. The load yield of EFV in F127COOH-EFV nanodrug formulation was close to 100% determined by HPLC assay.

As shown in FIG. 1A, Pluronics are block copolymers that consist of hydrophilic polyethylene oxide (PEO) and hydrophobic polypropylene oxide (PPO) blocks arranged in a basic PEOx-PPOy-PEOx structure (where "x" and "y" represent the repeated number of times ethylene oxide [EO] and propylene oxide [PO] are in the structure, respectively). F127 can easily form as core/shell nanoparticles in an aqueous solution by a simple hydration technique and its hydrophobic core can act as an accommodation for a lipophilic drug. In this spontaneously formed core-shell structure, poorly soluble drugs can be incorporated into the hydrophobic core and protected from inactivation in biological media. Further, the outside, hydrophilic layer can provide the micellar system with advantages, such as increasing drug solubility, circumventing reticuloendothelial system (RES) uptake, improving circulation time, enhanced permeability and retention (EPR) effect[3]. It has been reported to exhibit an acceptable safety profile with a maximum tolerated dose of 70 mg/m² with sustained drug release and clearance profile with comparison to conventional formulation[30,31].

To improve the target efficiency, a new type of F127 with a functional group is produced by surface chemical modification. In one embodiment, carboxyl groups were introduced on the PEO terminal of F127 (the product of carboxylated F127 is abbreviated as F127COOH) for the purpose of bio-conjugation via gentle esterification with maleic anhydride.

By a typical micelles preparation process, EFV encapsulated in carboxyl-functionalized amphiphilic polymers results in stable, micelle-like structures due to the strong hydrophobic interactions between native hydrophobic EFV and the PPO hydrocarbon chains (from hydrophobic section of F127) to foul' F127COOH-EFV nanoparticles.

Anti-GP2 antibodies were conjugated with carboxyl groups on the surface of F127 via the formation of active amino intermediate group (FIG. 1B). Being a very specific monoclonal antibody designed for human M-cells, anti-GP2 antibody targets the nanodrugs towards M-cells located at the GALT[32,33].

The degree of maleic acid substitution onto F127 was ~1.5 mol %. The yield of F127COOH in this synthesis was measured to be above 85% by acid-base titration, and no significant degradation of the copolymer was found. The critical micelle concentration (CMC) determined the stability of micelles against possible dilution of the micellar system in bodily fluids. To this end, the CMC of F127COOH nanoparticles was $4.7 \times 10^{-7}$ M, which indicates extreme stability after dilution. The size of F127COOH-EFV nanodrug formulation in aqueous media was around 140 nm with excellent mono-dispersion under TEM measurement, shown in FIG. 2A.

The hydrodynamic size in aqueous dispersion by method of Dynamic Laser Scattering (DLS) has high consistence with TEM results, which was around 140 nm with 0.12 polydispersion Index (PDI). In general, the value of PDI less than 0.3 is recognized as narrow size distribution for particles. The shape and the size were not significantly altered after conjugation with anti-GP2 antibodies. The TEM analysis indicated that no aggregation occurred during the conjugation process. The surface charge of F127COOH-EFV nanodrug formulation was 19.38±2.2 mV by zeta potential measurement. Vectorization of the nanocarriers with antibodies did not affect the surface charge and had negligible change of the particles.

The DLS technique was also used to measure the hydrodynamic size distribution and colloidal stability of the F127COOH-EFV in PBS. As displayed in FIG. 2B, the DLS results showed that the average hydrodynamic radius of the F127COOH-EFV to be 128.8±15.6 nm (PDI=0.10) over two weeks. The surface charges of F127COOH-EFV nanodrug formulation were not significantly changed with, or without antibodies conjugation based on the DLS measurements. The mimic stability evaluation in blood fluid also found to be stable by measuring their size in an in vitro closed circulatory system at 37° C. for up to 28 h (viscosity: 4.5 cP)[19]. The time-dependent changes in hydrodynamic diameter of the F127COOH-EFV with antibodies conjugation were less than 10% under the PBS (p117.4) and 0.005% pepsin solution (pH 6.8) (FIGS. 3A & 3B), indicating that these nanoparticles have well colloidal stability for a quite long term in a blood physiological condition and intestine enzymatic circumstance.

Generally, the stability test on nanodrug under gut circumstance is critical for the full understanding of the characterization and fate of particles applied in in vivo and the potential clinic. In one embodiment, this nanodrug will be finally encapsulated into an enteric coated capsule for oral administration in animal. This enteric surface coating endows capsule with stability at highly acidic pH (e.g. in stomach), and breaks down rapidly at around pH 6.8 (e.g. in intestine) to release the drug.

In order to find out hydrodynamic size variation of F127COOH-EFV nanodrug under intestine conditions (0.005% pepsin solution, pH 6.8), DLS size of particles was monitored against time for up to seven days. The results showed that fluctuation of particle diameter was less than 10%, which is almost the same as the variation extent in water (FIG. 3B). This confirms the stability of nanoformulation under intestine enzymatic circumstance.

Because drug release from the nanoformulation follows a diffusion mechanism, with intact shape and structure under intestine enzymatic circumstance, the loaded efavirenz (EFV) may release at targeted site and time once the nanoformulation is encapsulated into an enteric coated capsule.

Example 2—Sustained Drug Release of Nanodrug

To analyze the drug release profile, F127COOH-EFV was subjected to dissolution test. In complying with sink condition from FDA requirement on drug product dissolution, F127COOH-EFV in PBS (pH 7.4) was placed in the dialysis bag using composition of: 0.1% Tween 20 aqueous solution as dissolution solution at 37° C.[34]. The released drug outside of dialysis bag were sampled at different time intervals (from 5 min up to 14 days) and were assayed by HPLC[35].

The data indicated that 80% of drug was released from the Pluronic particles over 6 days. As shown in FIG. 4, the $t_{1/2}$ of EFV in F127COOH-EFV nanodrug formulation was about 48 h ($t_{1/2}$=48 h). This was considerably longer than the release of free drug ($t_{1/2}$=8 h).

Example 3—Cytotoxicity of Nanodrug on M-Cells

Lymphatic uptake of nanoparticle, retention and sustain release of the drug at the GALT depends mainly on the size, shape and surface characterization of the nanoparticle. Generally, smaller particles have better lymphatic uptake than larger particles with lower retention capability[2,38-40]. In this regard, steric stabilization with hydrophilic polymer like F127COOH can improve the uptake of EFV by lymph nodes and increase their stabilization inside them. Lymph node retention of micellular drug has been investigated by other researchers in cancer therapy[41]. However, it had limited success due to poor loading capacity and toxicity issue[42]. In order to address this issue, we carried out cytotoxicity studies of this nanodrug (FIG. 5).

In this regard, MTS assay was performed to evaluate the cytotoxicity of nanodrug in Caco-2 cells and primary human macrophages, respectively, as per published protocol[43]. The results indicated that the nanodrug did not significantly affect the cell viability over 24 hrs incubation with Caco-2 cells at nanodrug concentration of 0.1 mg/ml to 10 mg/ml (FIG. 5A). Even in case of primary human macrophage, effect of nanodrug on cell viability did not decrease significantly up to the concentration of 100 ug/ml (FIG. 5B). Both observations indicated that there was no immediate cellular toxicity of nanodrug on human cell line (Caco-2) and primary human cells (macrophages) at the tested concentrations. Taking into account the high drug loading capacity and cellular toxicity, high drug concentrations (above 10 mg/ml) were not considered for further evaluations. Along the same line, the ratio of drug and polymer was also optimized in Caco-2 and Raji cells in order to get the maximum drug activity. As a result, 0.07 mg/ml of nanodrug was used for further in vitro characterization.

Example 4—Effect of Nanodrug in ROS Production in Caco-2 Cells

Tests were also conducted to determine whether the nanodrug itself causes oxidative stress to the cellular environment after treatment, which may affect cellular metabolism. In this regard, cells were treated with different concentration of nanodrug in order to observe the effect of this formulation on ROS production.

As shown in the FIG. 6, the nanodrug did not induce any significant ROS production with the treatment as high as 10 mg/ml. This observation indicated that the current formulation did not cause any oxidative stress to Caco-2 cells post treatment. Thus, it was further assuring the nontoxicity of the nanodrug for cellular treatment.

Example 5—Characterization of M-Cells in Co-Culture Model

In the co-culture model Caco-2 cells developed M-cells-like morphology after incubation with Raji cells. In order to investigate the transformation of Caco-2 cells to M-cell, a flow-cytometry analysis was done with M-cell specific anti-GP2 antibodies (GP2)[44,45]. Monoculture of Caco-2 cells was used for this study as a negative control. The data indicated that 14% of the Caco-2 cells developed M-cells-like characteristics upon the co-culturing with Raji cells (FIG. 7), whereas, there was no M-cell characters observed in monoculture of Caco-2 cells. Thus the transformations of M-cell from Caco-2 cells were clearly observed through this analysis.

In order to confirm this observation, further characterization of M-cells was done through immunocytochemistry with anti-GP2 antibodies. The cells were grown and co-cultured as mentioned above and at the end of incubation cells were stained with anti-GP2 antibodies. The fluorescent image analysis indicated that the presence of anti-GP2 antibodies was significantly higher in M-cells compared to Caco-2 cells alone as explained in FIG. 8.

Example 6—Assessment of Model Functionality by Fluorescent Nanodrugs (FND) Transport In order to monitor the functional activity of M-cell in in vitro, a transport study of Alexa Fluor 610-X NHS conjugated nanodrug or FND was designed and monitored the transport rate in mono (Caco-2) and co-culture (M-Cell) model. These FND formulations were further conjugated with anti-GP2 antibodies (FND-GP2). The FND and FND-GP2 were added apically and incubated for 2 h at 37° C. After the incubation, part of the trans-wells were used for fluorescent microscopy studies to observe FND accumulation and a parallel set of trans-wells were kept to monitor the FND transport from apical to basolateral site. The microscopic analysis indicated FND-GP2 was more accumulated in the M-cells at greater extent than FND. At the same time, the Caco-2 cells treated with FND and FND-GP2 accumulated significantly less fluorescence than M-cell FIG. 9A.

Noteworthy, both M-cells and Caco-2 cells showed a sustained uptake of FND in the external medium. The measurement of FND uptake on basolateral side of trans-well was done by measuring the fluorescence. The nanodrug uptake was measured in terms of fluorescence with respect to time up to 48 hrs. Along with higher accumulation levels, the prolonged drug release characteristics from M-cells was demonstrated compared to Caco-2 cells, indicating the superior role of M-cell for drug delivery (FIG. 9B).

Example 7—Anti-HIV Activity of Nanodrug

Anti-HIV activity of the nanodrug against HIV was tested in primary human macrophages and in vitro M-cell model. Human macrophages were infected with HIV-1 for 24 hrs and then treated with nanodrug or EFV separately. Nanodrug treatment data indicated that there was consistent viral inhibition up to day 10 and beyond. Whereas free EFV treated cells showed immediate inhibition of viral replication on day 1 and following that there was increase of viral p24 level indicating gradual loss of anti-viral activity of EFV. At the end of the experiment (day 10), effect of EFV treatment significantly decreased and p24 level increased up to the level of untreated cells. In this regard, untreated and HIV-1 infected macrophages were served as a positive control which showed gradual increase of p24 level up to day 10 indicating unaffected HIV-1 replication in macrophages (FIG. 10A).

In order to observe anti-HIV activity of nanodrug in M-cell model, Raji cells were infected with HIV and cultured with Caco-2 cells. They were further treated separately with nanodrug or EFV for up to 10 days at a same concentration. Viral p24 protein level was measured in culture supernatant at different time points. In the case of nanodrug, p24 protein level did not change up to day two. However, from day 3 to day 10 there was a significant decrease in viral replication when compared to EFV treated cells. Compared to nanodrug, EFV treatment resulted in an immediate reduction of viral replication, but p24 level increased closer to the level of untreated cells within day 10 indicating viral rebound in the cells (FIG. 10B). As a positive control, p24 level of HIV infected Raji cells were observed up to day 10.

At the end of two experiments, the primary infection of HIV-11Ba-L in both Raji and macrophages was confirmed by HIV-LTR R/U5 gene PCR. The data represented in TAI values in both cells indicated that both cell types were successfully infected with HIV and presented an optimum challenge to test the nanodrug in evaluating its Anti-HIV activity (FIG. 10C).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The description herein of any aspect or embodiment of the invention using terms such as "comprising," "having," "including" or "containing" with reference to an element or elements is intended to provide support for a similar aspect or embodiment of the invention that "consists of," "consists essentially of," or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The term "consisting essentially of," as used herein, limits the scope of the ingredients and steps to the specified materials or steps and those that do not materially affect the basic and novel characteristic(s) of the present invention, i.e., compositions and methods for targeting medications to M-cells and/or treating HIV.

REFERENCES

1. Best B M, Letendre S L, Brigid E, et al; CHARTER Group. Low atazanavir concentrations in cerebrospinal fluid. *AIDS*. 2009; 23(1):83-87.

2. Ding H, Wu F, Nair M P. Image-guided drug delivery to the brain using nanotechnology. *Drug Discov Today.* 2013; 18(21-22):1074-1080.
3. Dane K Y, Nembrini C, Tomei A A, et al. Nano-sized drug-loaded micelles deliver payload to lymph node immune cells and prolong allograft survival. *J Control Release.* 2011; 156(2):154-160.
4. Kanmogne G D, Singh S, Roy U, et al. Mononuclear phagocyte intercellular crosstalk facilitates transmission of cell-targeted nanoformulated antiretroviral drugs to human brain endothelial cells. *Int J Nanomedicine.* 2012; 7:2373-2388.
5. Lerner P, Guadalupe M, Donovan R, et al. The gut mucosal viral reservoir in HIV-infected patients is not the major source of rebound plasma viremia following interruption of highly active antiretroviral therapy. *J Virol.* 2011; 85(10):4772-4782.
6. Varatharajan L, Thomas S A. The transport of anti-HIV drugs across blood-CNS interfaces: summary of current knowledge and recommendations for further research. *Antiviral Res.* 2009; 82(2):A99-A109.
7. Pilakka-Kanthikeel S, Atluri V S, Sagar V, Saxena S K, Nair M. Targeted brain derived neurotropic factors (BDNF) delivery across the blood-brain barrier for neuroprotection using magnetic nano carriers: an in-vitro study. *PLoS One.* 2013; 8(4):e62241.
8. Roy U, Bulot C, Honer zu Bentrup K, Mondal D. Specific increase in MDR1 mediated drug-efflux in human brain endothelial cells following co-exposure to HIV-1 and saquinavir. *PLoS One.* 2013; 8(10):e75374.
9. Hondo T, Kanaya T, Takakura I, et al. Cytokeratin 18 is a specific marker of bovine intestinal M cell. *Am J Physiol Gastrointest Liver Physiol.* 2011; 300(3):G442-G453.
10. Kemeis S, Bogdanova A, Kraehenbuhl J-P, Pringault E. Conversion by Peyer's patch lymphocytes of human enterocytes into M cells that transport bacteria. *Science.* 1997; 277(5328):949-952.
11. Gullberg E, Leonard M, Karlsson J, et al. Expression of specific markers and particle transport in a new human intestinal M-cell model. *Biochem Biophys Res Commun.* 2000:279(3):808-813.
12. Manocha M, Pal P C, Chitralekha K T, et al. Enhanced mucosal and systemic immune response with intranasal immunization of mice with HIV peptides entrapped in PLG microparticles in combination with Ulex Europaeus-I lectin as M cell target. *Vaccine.* 2005; 23(48-49): 5599-5617.
13. des Rieux A, Ragnarsson E G, Gullberg E, Preat V, Schneider Y J, Artursson P. Transport of nanoparticles across an in vitro model of the human intestinal follicle associated epithelium. *Eur J Pharm Sci.* 2005; 25(4-5): 455-465.
14. Dhoro M, Zvada S, Ngara B, et al. CYP2B6*6, CYP2B6*18, body weight and sex are predictors of efavirenz pharmacokinetics and treatment response: population pharmacokinetic modeling in an HIV/AIDS and TB cohort in Zimbabwe. *BMC Pharmacol Toxicol.* 2015; 16:4.
15. Olagunju A, Bolaji O, Amara A, et al. Breast milk pharmacokinetics of efavirenz and breastfed infants' exposure in genetically-defined subgroups of mother-infant pairs: an observational study. *Clin Infect Dis.* 2015; 61(3):453-463.
16. Martin A S, Gomez A I, Garcia-Berrocal B, et al. Dose reduction of efavirenz: an observational study describing cost-effectiveness, phaimacokinetics and pharmacogenetics. *Pharmacogenomics.* 2014; 15(7):997-1006.
17. Ding H, Yong K-T, Law W-C, et al. Non-invasive tumor detection in small animals using novel functional Pluronic nanomicelles conjugated with anti-mesothelin antibody. *Nanoscale.* 2011; 3(4):1813-1822.
18. Ding H, Yong K-T, Roy I, et al. Bioconjugated PLGA-4-arm-PEG branched polymeric nanoparticles as novel tumor targeting carriers. *Nanotechnology.* 2011; 22(16): 165101.
19. Ding H, Sagar V, Agudelo M, et al. Enhanced blood-brain barrier transmigration using a novel transferrin embedded fluorescent magneto-liposome nanoformulation. *Nanotechnology.* 2014; 25(5):055101. doi: 10.1088/0957-4484/25/5/055101(5).
20. Gandhi N, Saiyed Z M, Napuri J, et al. Interactive role of human immunodeficiency virus type 1 (HIV-1) Glade-specific Tat protein and cocaine in blood-brain barrier dysfunction: implications for HIV-1-associated neurocognitive disorder. *J Neurovirol.* 2010; 16(4):294-305.
21. Wu F, Bhansali S G, Tamhane M, et al. Noninvasive real-time fluorescence imaging of the lymphatic uptake of BSA-IRDye 680 conjugate administered subcutaneously in mice. *J Pharm Sci.* 2012; 101(5):1744-1754.
22. Agudelo M. Gandhi N, Saiyed Z, et al. Effects of alcohol on histone deacetylase 2 (HDAC2) and the neuroprotective role of trichostatin A (TSA). *Alcohol Clin Exp Res.* 2011; 35(8):1550-1556.
23. Schmidtmayerova H, Alfano M, Nuovo G, Bukrinsky M. Human immunodeficiency virus type 1 T-lymphotropic strains enter macrophages via a CD4- and CXCR4-mediated pathway: replication is restricted at a post entry level. *J Virol.* 1998; 72(6):4633-4642.
24. Atluri V S, Kanthikeel S P, Reddy P V, Yndart A, Nair M P. Human synaptic plasticity gene expression profile and dendritic spine density changes in HIV-infected human CNS cells: role in HIV-associated neurocognitive disorders (HAND). *PLoS One.* 2013; 8(4):e61399.
25. Atluri V S, Pilakka-Kanthikeel S, Samikkannu T, et al. Vorinostat positively regulates synaptic plasticity genes expression and spine density in HIV infected neurons: role of nicotine in progression of HIV-associated neurocognitive disorder. *Mol Brain.* 2014; 7:37.
26. Yang S P, Liu W C, Lee K Y, et al. Effectiveness of a reduced dose of efavirenz plus 2 NRTIs as maintenance antiretroviral therapy with the guidance of therapeutic drug monitoring. *J Int AIDS Soc.* 2014; 17(4 Suppl 3):19524.
27. Hurst S J, Eifler A, Thaxton C S. Nanoparticle therapeutics: FDA approval, clinical trials, regulatory pathways, and case study. *Methods Mol Biol.* 2011; 726:325-338.
28. Elluru M, Ma H, Hadjiargyrou M, Hsiao B S, Chu B. Synthesis and characterization of biocompatible hydrogel using Pluronics-based block copolymers. *Polymer.* 2013; 54(8):2088-2095.
29. Simon T, Boca S, Biro D, Baldeck P, Astilean S. Gold-Pluronic core-shell nanoparticles: synthesis, characterization and biological evaluation. *J Nanopart Res.* 2013; 15(4):1-8.
30. Chen L, Sha X, Jiang X, Chen Y, Ren Q, Fang X. Pluronic P105/F127 mixed micelles for the delivery of docetaxel against Taxol-resistant non-small cell lung cancer: optimization and in vitro, in vivo evaluation. *Int J Nanomedicine.* 2013; 8:73-84.

31. Oerlemans C, Bult W, Bos M, Storm G, Nijsen J F, Hennink W. Polymeric micelles in anticancer therapy: targeting, imaging and triggered release. *Pharm Res.* 2010; 27(12):2569-2589.
32. Hase K, Kawano K, Nochi T, et al. Uptake through glycoprotein 2 of FimH+ bacteria by M cells initiates mucosal immune response. *Nature.* 2009; 462(7270):226-230.
33. Kunisawa J, Kurashima Y, Kiyono H. Gut-associated lymphoid tissues for the development of oral vaccines. *Adv Drug Deliv Rev.* 2012; 64(6):523-530.
34. Wallace S J, Li J, Nation R L, Boyd B J. Drug release from nanomedicines: selection of appropriate encapsulation and release methodology. *Drug Deliv Trans' Res.* 2012; 2(4):284-292.
35. Hua S. Comparison of in vitro dialysis release methods of loperamide-encapsulated liposomal gel for topical drug delivery. *Int J Nanomedicine.* 2014; 9:735-744.
36. Du B, Li Y, Li X, Youmei A, Chen C, Zhang Z. Preparation, characterization and in vivo evaluation of 2-methoxyestradiol-loaded liposomes. *Int J Pharm.* 2010; 384(1-2):140-147.
37. Li S, Hu J, Zhang L, et al. In-vitro and in-vivo evaluation of austocystin D liposomes. *J Pharm Pharmacol.* 2013; 65(3):355-362.
38. Reddy S T, Rehor A, Schmoekel H G, Hubbell J A, Swartz M A. In vivo targeting of dendritic cells in lymph nodes with poly(propylene sulfide) nanoparticles. *J Control Release.* 2006; 112(1):26-34.
39. Ding H, Wu F. Image guided biodistribution and pharmacokinetic studies of theranostics. *Theranostics.* 2012; 2(11):1040-1053.
40. Ding H, Wu F. Image guided biodistribution of drugs and drug delivery. *Theranostics.* 2012; 2(11):1037-1039.
41. Tan R, Niu M, Zhao J, Liu Y, Feng N. Preparation of vincristine sulfate-loaded poly (butylcyanoacrylate) nanoparticles modified with pluronic F127 and evaluation of their lymphatic tissue targeting. *J Drug Target.* 2014; 22(6):509-517.
42. Torchilin V P. Multifunctional nanocarriers. *Adv Drug Deliv Rev.* 2006; 58(14):1532-1555.
43. Ding H. Yong K-T, Roy I, et al. Gold nanorods coated with multilayer polyelectrolyte as contrast agents for multimodal imaging. *J Phys Chem C.* 2007; 111(34): 12552-12557.
44. Tahoun A, Mahaj an S, Paxton E, et al. Salmonella transforms follicle-associated epithelial cells into M cells to promote intestinal invasion. *Cell Host Microbe.* 2012; 12(5):645-656.
45, Oikonomou E, Makrodouli E, Evagelidou M, Joyce T, Probert L, Pintzas A. BRAF(V600E) efficient transformation and induction of microsatellite instability versus KRAS(G12V) induction of senescence markers in human colon cancer cells. *Neoplasia.* 2009; 11(11):1116-1131.
46. Haney M J, Suresh P, Zhao Y, et al. Blood-borne macrophage-neural cell interactions hitchhike on endosome networks for cell-based nanozyme brain delivery. *Nanomedicine (Loud).* 2012; 7(6):815-833.
47. Yuki Y, Nochi T, Kiyono I I. Progress towards an AIDS mucosal vaccine: an overview. *Tuberculosis (Edinb).* 2007; 87(suppl 1):S35-S4

The invention claimed is:

1. A pharmaceutical composition comprising a nanodrug that comprises an active agent, a poloxamer, and an antibody to glycoprotein-2 (GP2) or antibody fragment to GP2 that targets microfold cells (M-cells) and facilitates the uptake of the nanodrug by M-cells.

2. The pharmaceutical composition, according to claim 1, in which the poloxamer is F127COOH.

3. The pharmaceutical composition, according to claim 2, having F127COOH conjugated to GP2.

4. The pharmaceutical composition, according to claim 1, comprising a retroviral agent as the active agent.

5. The pharmaceutical composition, according to claim 4, wherein the retroviral agent is efavirenz.

6. The pharmaceutical composition, according to claim 1, comprising a latency activating drug.

7. The pharmaceutical composition, according to claim 1, wherein the nanodrug is encapsulated in an enteric coating that resists degradation at pHs below 5.0 and releases the nanodrug at a pH above 5.0.

8. A method of delivering an active agent to gut-associated lymphoid tissue (GALT) comprising administering, to a subject, a pharmaceutical composition comprising a nanodrug that comprises an active agent, a poloxamer, and an antibody to GP2 or antibody fragment to GP2 that targets M-cells and facilitates the uptake of the nanodrug by M-cells.

9. The method, according to claim 8, used to deliver a retroviral drug directly to GALT and beyond.

10. The method, according to claim 8, wherein a sustained release of the active agent occurs.

11. The method, according to claim 8, used to treat HIV in the subject.

12. The method, according to claim 8, in which the poloxamer is F127COOH.

13. The method, according to claim 8, wherein the subject is a human or mouse and the composition is administered intravenously, intraperitoneally, or subcutaneously.

14. The method, according to claim 9, wherein the retroviral drug is efavirenz.

15. The method, according to claim 8, wherein the pharmaceutical composition comprises a latency activating drug.

16. The method, according to claim 8, wherein the nanodrug is encapsulated in an enteric coating that resists degradation at pHs below 5.0 and releases the nanodrug at a pH above 5.0.

17. A pharmaceutical composition comprising a nanodrug comprising efavirenz and F127COOH conjugated to anti-GP2 antibody that facilitates the uptake of the nanodrug by M-cells, and wherein the nanodrug is coated with an enteric coating that degrades only at a pH above 5.0.

18. A method of delivering an active agent to gut-associated lymphoid tissue (GALT) comprising administering, to a subject, a pharmaceutical composition comprising a nanodrug comprising a F127COOH micelle conjugated to anti-GP2 antibody that facilitates the uptake of the F127COOH micelle by M-cells, and further comprising efavirenz encapsulated in the F127COOH micelle, characterized in that the nanodrug is coated with an enteric coating that degrades only at a pH above 5.0.

19. The method, according to claim 18, in which the F127COOH micelle has a size of 120-140 nm.

* * * * *